US010813939B2

(12) United States Patent
Sotomayor et al.

(10) Patent No.: US 10,813,939 B2
(45) Date of Patent: Oct. 27, 2020

(54) BROMODOMAIN INHIBITOR AS ADJUVANT IN CANCER IMMUNOTHERAPY

(71) Applicants: H. LEE MOFFITT CANCER CENTER AND RESEARCH INSTITUTE, INC., Tampa, FL (US); DANA-FARBER CANCER INSTITUTE, INC., Boston, MA (US)

(72) Inventors: Eduardo M. Sotomayor, Tampa, FL (US); James Bradner, Weston, MA (US); Jianguo Tao, Tampa, FL (US)

(73) Assignees: H. Lee Moffitt Cancer Center and Research Institute, Inc., Tampa, FL (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/533,168

(22) PCT Filed: Dec. 4, 2015

(86) PCT No.: PCT/US2015/063928
§ 371 (c)(1),
(2) Date: Jun. 5, 2017

(87) PCT Pub. No.: WO2016/090219
PCT Pub. Date: Jun. 9, 2016

(65) Prior Publication Data
US 2017/0360801 A1 Dec. 21, 2017

Related U.S. Application Data

(60) Provisional application No. 62/088,327, filed on Dec. 5, 2014, provisional application No. 62/106,885, filed on Jan. 23, 2015.

(51) Int. Cl.
| | | |
|---|---|---|
| A61K 31/5517 | (2006.01) | |
| A61K 39/39 | (2006.01) | |
| A61K 39/395 | (2006.01) | |
| A61K 45/06 | (2006.01) | |
| C12N 5/0783 | (2010.01) | |
| A61K 39/00 | (2006.01) | |

(52) U.S. Cl.
CPC .......... *A61K 31/5517* (2013.01); *A61K 39/39* (2013.01); *A61K 39/39558* (2013.01); *A61K 45/06* (2013.01); *C12N 5/0636* (2013.01); *A61K 2039/55511* (2013.01); *C12N 2501/999* (2013.01); *C12N 2502/11* (2013.01)

(58) Field of Classification Search
CPC .............. A61K 31/5517; C12N 5/0636; C12N 5/0638; C12N 2501/999; C12N 2502/11
See application file for complete search history.

(56) References Cited

U.S. PATENT DOCUMENTS

| | | | |
|---|---|---|---|
| 2004/0175369 A1* | 9/2004 | Yu | A61K 39/0011 424/93.21 |
| 2012/0220573 A1 | 8/2012 | Gosmini | |
| 2014/0256706 A1 | 9/2014 | Wang | |
| 2016/0158207 A1* | 6/2016 | Adler | A61K 45/06 514/213.01 |

FOREIGN PATENT DOCUMENTS

| | | | |
|---|---|---|---|
| EA | 020390 B1 | 10/2014 | |
| WO | WO-2011143669 A2 * | 11/2011 | ........... C07D 487/04 |
| WO | 2014/164771 A1 | 10/2014 | |
| WO | 2014164596 A1 | 10/2014 | |
| WO | 2015/070020 A2 | 5/2015 | |
| WO | WO-2015120198 A1 * | 8/2015 | ......... A61K 39/0011 |
| WO | 2016/050821 A1 | 4/2016 | |

OTHER PUBLICATIONS

Abstract of Peethambaram et al (Journal of Clinical Oncology, 2004, vol. 22, No. 14, suppl., Abstract No. 2528) (Year: 2004).*
Ott et al (Blood, 2012, vol. 120, pp. 2843-2852) (Year: 2012).*
Abstract of Valenta et al (Blood, 2013, vol. 122, No. 21, Abstract No. 2842) (Year: 2013).*
Abstract of Jochems et al (Cancer Research, 2013, vol. 73, No. 8, Supp.1, Abstract No. 498) (Year: 2013).*
Pardoll (Nature Reviews Cancer, 2012, vol. 12, pp. 252-264) (Year: 2012).*
International Search Report and Written Opinion issued in International Application No. PCT/US15/063928, dated Apr. 4, 2016.
International Preliminary Report on Patentability issued in Application No. PCT/US15/063928, dated Jun. 15, 2017.
Mele, D. et al. BET Bromodomain Inhibition Suppresses TH17-Mediated Pathology. J. Exp Med. 2013, vol. 210, No. 11, pp. 22181-22190; abstract; p. 2182, third paragraph; p. 2189, seventh paragraph.
Emadali, A. et al. Identification of a Novel BET Bromodomain Inhibitor-Sensitive, Gene Regulatory Circuit That Controls Rituximab Response and Tumour Growth in Aggressive Lymphoid Cancers. EMBO Mol. Med. 2013, vol. 5, pp. 1180-1195; abstract; p. 1188, first paragraph; p. 1190, paragraph continued from p. 1189; p. 1192, seventh paragraph.
Trabucco, S. et al. Inhibition of Bromodomain Proteins for the Treatment of Human Diffuse Large B-Cell Lymphoma. Clin. Cancer Res. E. pub Jul. 9, 2014, pp. 113-122; abstract.

(Continued)

*Primary Examiner* — Karen A. Canella
(74) *Attorney, Agent, or Firm* — Meunier Carlin & Curfman LLC

(57) ABSTRACT

Inhibition of bromodomain proteins in antigen presenting cells is shown herein to be more inflammatory, to display lower expression of the immunosuppressive molecule PDL1, and to be capable of restoring the responsiveness of tolerant T-cells. Therefore, disclosed is a method for promoting T-cell activation during cancer immunotherapy in a subject that involves administering to a subject undergoing cancer immunotherapy a composition comprising a bromodomain inhibitor. Also disclosed is a method for treating cancer in a subject, comprising co-administering to the subject a bromodomain inhibitor and an immunostimulatory agent.

3 Claims, 5 Drawing Sheets

(56) References Cited

OTHER PUBLICATIONS

Hoel, H. Ex Vivo Expansion Protocol for Human Turner Specific T. Cells for Adoptive T Cell Therapy. Journal of Immunological Methods. Feb. 2010, pp. 52-60; abstract; p. 54, second and fourth paragraphs; p. 56, first and third paragraphs; p. 59, second paragraph.
Wolfle, S. et al. PD-L1 Expression on Tolerogenic APCs Is Controlled by STAT-3. Eur. J. Immunol. 2011, vol. 42, pp. 413-424; abstract.
Cheng, F. et al. A Critical Role for Stat3 Signaling in Immune Tolerance, Immunity, Sep. 2003, vol. 19, pp. 125-436; p. 425, fifth paragraph.
Search Report and Written Opinion issued for Singaporean Application No. 1120704089U, dated, May 8, 2018.
Extended European Search Report issued for European Application No. 15864653.9, dated Jun. 27, 2018.
Yuki Kagoya, et al., "BET bromodomain inhibition enhances T cell persistence and function in adoptive immunotherapy models", J Clin Invest. Sep. 1, 2016; 126(9): 3479-3494. Published online Aug. 22, 2016. doi: 10.1172/JCI86437.
Notice of Reasons for Refusal issued for Japanese Application No. 2017-548371, dated Nov. 19, 2019.
Okamoto et al., Abstract No. 5033: Down-regulation of PD-1 ligands by chemotherapeutic agent via inhibition of STAT3 activity enhances T cell-stimulating ability of dendritic cell. Cancer Research, 2014, vol. 74, No. 19, supplement.
Vasir, et al., Abstract No. 3217: STAT3 inhibition promotes potent Th1 responses by down regulating Pdl-1 expression an tumor cells. Blood 2013 vol. 122:3217.
Ray, et al. Inducible STAT3 NH2 terminal mono-ubiquitination promotes BRD4 complex formation to regulate apoptosis. Cellular signalling 26.7 (2014): 1445-1455.
Hayakawa, Taeko, et al. Enhanced anti-tumor effects of the PD-1/PD-L1 blockade by combining a highly absorptive form of NF-kB/STAT3 inhibitor curcumin. Journal for immunotherapy of cancer 2.S3 (2014): P210.
Allen, et al., A role of immunotherapy in metastatic malignant melanoma. Central Nervous System Agents in Medicinal Chemistry 2012, vol. 12, p. 182-188.
Kujawski, et al., Targeting STAT3 in adoptively transferred T cells promotes their in vivo expansion and antitumor affects. Cancer research 70.23 (2010): 9599-9610.
Rasmussen A.M. et al. Ex vivo expansion protocol for human tumor specific T cells for adoptive T cell therapy // Journal of immunological methods, 2010, vol. 355, N. 1-2., pp. 52-60.
Wang, H. et al., JQ 1, a Selective Bromodomain Inhibitor, Decreased the Expression of the Tolerogenic Molecule PDL1 in Antigen-Presenting Cells (APCs) and Restores the Responsiveness of Anergic CD4+ T Cells. Blood, Dec. 4, 2014, vol. 124, No. 21, pp. 2749. Abstract.
Second Written Opinion issued in Singapore Application 11201704089U, dated Sep. 13, 2019.
Office Action and Search Report issued in Russian Application No. 2017121025, dated Jul. 5, 2019.
Communication Pursuant to Article 94(3) EPC issued for Application No. 15864653.9, dated Nov. 18, 2019.
Wang Lan, Henan "Basics of Pathogen Biology and Immunology", Science and Technology Press, p. 42 of the text "Antigen Presenting Cells", Aug. 2012. Translation not available.
Office Action issued for Chinese Application No. 2015800721065, dated May 22, 2020.

* cited by examiner

BROMODOMAIN INHIBITOR AS ADJUVANT IN CANCER IMMUNOTHERAPY

CROSS-REFERENCE TO RELATED APPLICATIONS

This application is a National Phase Application of PCT/US2015/063928, filed Dec. 4, 2015, which claims the benefit of U.S. Provisional Application No. 62/088,327, filed Dec. 5, 2014, and Application Ser. No. 62/106,885, filed Jan. 23, 2015, which are hereby incorporated herein by reference in their entirety.

BACKGROUND

Immunotherapy has become an increasingly appealing therapeutic strategy for patients with cancer, with many late-stage clinical trials demonstrating overall survival (OS) advantages in melanoma and castration-resistant prostate cancer. More recently, non-small cell lung cancer (NSCLC) has become a focus for the next generation of immune-based therapeutic strategies. Immunotherapy, in particular the use of monoclonal antibodies that block inhibitory immune checkpoint molecules and therefore enhance the immune response to tumors, has shown clinical promise in advanced solid tumors.

Immune checkpoints refer to a plethora of inhibitory pathways hardwired into the immune system that are crucial for maintaining self-tolerance and modulating the duration and amplitude of physiological immune responses in peripheral tissues in order to minimize collateral tissue damage. It is now clear that tumors co-opt certain immune-checkpoint pathways as a major mechanism of immune resistance, particularly against T cells that are specific for tumor antigens.

Programmed death receptor-1 (PD-1) interaction with its ligands, PD-L1 and PD-L2, is one of the important strategies that many tumors employ to escape immune surveillance. Upon PD-Ls binding to PD-1, T cell receptor (TCR) signaling is dampened, causing inhibition of proliferation, decreased cytokine production, anergy and/or apoptosis. Thus expression of PD-Ls by tumor cells serves as a protective mechanism, leading to suppression of tumor-infiltrating lymphocytes in the tumor microenvironment.

SUMMARY

Antigen presenting cells treated with bromodomain inhibitors are shown herein to be more inflammatory, to display lower expression of the immunosuppressive molecule PDL1, and to be capable of restoring the responsiveness of tolerant T-cells. Therefore, disclosed is a method for promoting T-cell activation during cancer immunotherapy in a subject that involves administering to a subject undergoing cancer immunotherapy a composition comprising a bromodomain inhibitor. In some embodiments, the bromodomain inhibitor is a bromodomain and extraterminal ("BET") inhibitor. For example, the BET inhibitor can be (S)-tert-butyl 2-(4-(4-chlorophenyl)-2,3,9-trimethyl-6H-thieno[3,2-f][1,2,4]triazolo[4,3-a][1,4]diazepin-6-yl)acetate ("JQ1").

Also disclosed is a method for treating cancer in a subject, comprising co-administering to the subject a bromodomain inhibitor and an immunostimulatory agent. For example, the immunostimulatory agent can be an anti-PD-1 antibody, an anti-PD-L1 antibody, an anti-CTLA-4 antibody, or a combination thereof The method can further involve administering to the subject an immunogenic agent.

Also disclosed is a method for ex vivo activation and expansion of antigen-specific T cells for adoptive cell transfer (ACT). The method involves exposing a population of antigen presenting cells (APC) to a population of T lymphocytes in the presence of a bromodomain inhibitor. For example, the T lymphocytes can be selected from the group consisting of autologous tumor-infiltrating lymphocytes (TIL), T cells transduced with high-affinity T cell receptors (TCR), and T cells transduced with chimeric antigen receptors (CAR). Also as an example, APCs that can be used include autologous dendritic cells, macrophages, or a combination thereof In some cases, the the APCs are artificial antigen-presenting cells (aAPCs).

The details of one or more embodiments of the invention are set forth in the accompanying drawings and the description below. Other features, objects, and advantages of the invention will be apparent from the description and drawings, and from the claims.

DETAILED DESCRIPTION

Figure 1:
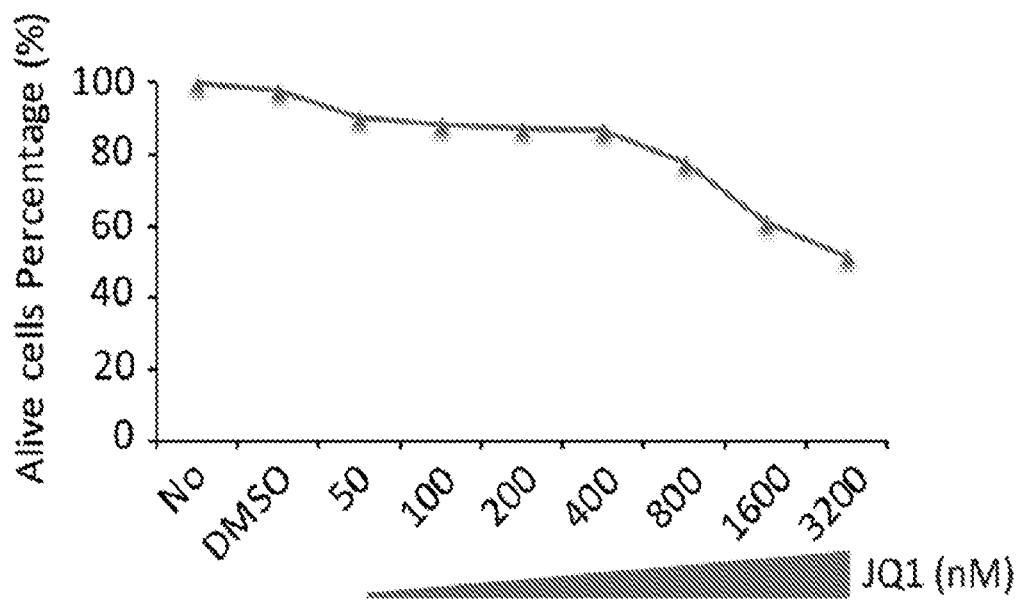
FIG. 1 shows PEM cell viability (%) as a function of JQ1 concentration (nM).

In some embodiments, the disclosed methods involve treating a subject in vivo using a bromodomain inhibitor such that growth of cancerous tumors is inhibited. A bromodomain inhibitor may be used alone to inhibit the growth of cancerous tumors. Alternatively, bromodomain inhibitor may be used in conjunction with other immunogenic agents, standard cancer treatments, or immunostimulatory agents.

There are also several treatment protocols that involve ex vivo activation and expansion of antigen specific T cells and adoptive transfer of these cells into recipients in order to promote antigen-specific T cells against tumor (Greenberg, R. & Riddell, S. (1999) Science 285: 546-51). These methods may also be used to activate T cell responses to infectious agents such as CMV. Ex vivo activation in the presence of a bromodomain inhibitor may be expected to increase the frequency and activity of the adoptively transferred T cells.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

Cancers whose growth may be inhibited by the disclosed methods include cancers typically responsive to immunotherapy. Non-limiting examples of cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Examples of other cancers that may be treated using the disclosed methods include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The disclosed methods may also be used in the treatment of metastatic cancers, especially metastatic cancers that express PD-L1.

In some embodiments, the bromodomain inhibitor can be combined with an immunogenic agent, such as cancerous cells, purified tumor antigens (including recombinant proteins, peptides, and carbohydrate molecules), or cells transfected with genes encoding immune stimulating cytokines. Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

The disclosed bromodomain inhibitor can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

The disclosed bromodomain inhibitor may be used in conjunction with a recombinant proteins and/or peptides expressed in a tumor in order to generate an immune response to these proteins. These proteins are normally viewed by the immune system as self-antigens and are therefore tolerant to them. The tumor antigen may also include the protein telomerase, which is required for the synthesis of telomeres of chromosomes and which is expressed in more than 85% of human cancers and in only a limited number of somatic tissues. Tumor antigen may also be "neo-antigens" expressed in cancer cells because of somatic mutations that alter protein sequence or create fusion proteins between two unrelated sequences or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity.

Dendritic cells (DC) are potent antigen presenting cells that can be used to prime antigen-specific responses. DC's can be produced ex vivo and loaded with various protein and peptide antigens as well as tumor cell extracts. DCs may also be transduced by genetic means to express these tumor antigens as well. DCs have also been fused directly to tumor cells for the purposes of immunization. As a method of vaccination, DC immunization may be effectively combined with a bromodomain inhibitor to activate more potent anti-tumor responses.

The disclosed bromodomain inhibitor may also be combined with standard cancer treatments, such as chemotherapeutic regimes. In these instances, it may be possible to reduce the dose of chemotherapeutic reagent administered.

An example of such a combination is a bromodomain inhibitor in combination with decarbazine for the treatment of melanoma. Another example of such a combination is a bromodomain inhibitor in combination with interleukin-2 (IL-2) for the treatment of melanoma. Other combination therapies that may result in synergy with bromodomain inhibitors through are radiation, surgery, and hormone deprivation. Each of these protocols creates a source of tumor antigen in the host. Angiogenesis inhibitors may also be combined with the bromodomain inhibitor. Inhibition of angiogenesis leads to tumor cell death which may feed tumor antigen into host antigen presentation pathways.

Bromodomain inhibitors are known in the art. A bromodomain inhibitor is any molecule or compound that can prevent or inhibit, in part or in whole, the binding of at least one bromodomain to acetyl-lysine residues of proteins (e.g., to the acetyl-lysine residues of histones). The bromodomain inhibitor may be any molecule or compound that inhibits a bromodomain as described above, including nucleic acids such as DNA and RNA aptamers, antisense oligonucleotides, siRNA and shRNA, small peptides, antibodies or antibody fragments, and small molecules such as small chemical compounds. It is to be understood that the bromodomain inhibitor may inhibit only one bromo-domain-containing protein or it may inhibit more than one or all bromodomain-containing proteins.

Examples of bromodomain inhibitors are described in JP 2009028043, JP 2009183291, WO 2011054843, WO 2011054848, W02009/084693A1, W02009084693, WO 2011054844, WO 2011054846, US 2012028912, Filippakopoulos et al. Bioorg Med Chem. 20(6): 1878-1886, 2012; Chung et al. J Med Chem. 54(11):3827-38, 2011; and Chung et al. J Biomol Screen. 16(10): 1170-85, 2011, which are incorporated herein by reference.

In some embodiments, the bromodomain inhibitor is a BET inhibitor. A BET inhibitor is any molecule or compound that can prevent or inhibit the binding of the bromodomain of at least one BET family member to acetyl-lysine residues of proteins. The BET inhibitor may be any molecule or compound that inhibits a BET as described above, including nucleic acids such as DNA and RNA aptamers, antisense oligonucleotides, siRNA and shRNA, small peptides, antibodies or antibody fragments, and small molecules such as small chemical compounds.

Examples of BET inhibitors are described in WO2011/143651, WO2009/084693, WO 2011/143669, WO 2011/143660, WO 2011/054851, and JP 2008156311, which are incorporated herein by reference. It is to be understood that a BET inhibitor may inhibit only one BET family member or it may inhibit more than one or all BET family members. Examples of BET inhibitors known in the art include, but are not limited to, RVX-208 (Resverlogix), PFI-1 (Structural Genomics Consortium), OTX015 (Mitsubishi Tanabe Pharma Corporation), BzT-Glaxo SmithKline).

In some aspects, the BET inhibitors is a compound of Formula I:

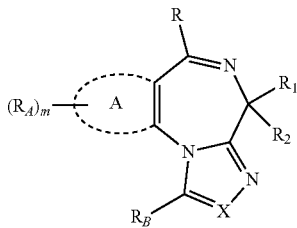

(I)

wherein
X is N or $CR_5$;
$R_5$ is H, alkyl, cycloalkyl, heterocycloalkyl, aryl, or heteroaryl, each of which is optionally substituted;
$R_B$ is H, alkyl, hydroxylalkyl, aminoalkyl, alkoxyalkyl, haloalkyl, hydroxy, alkoxy, or —COO—$R_3$, each of which is optionally substituted;
ring A is aryl or heteroaryl;
each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
R is alkyl, cycloalkyl, heterocycloalkyl, aryl, or heteroaryl; each of which is optionally substituted;
$R_1$ is —$(CH_2)_n$-L, in which n is 0-3 and L is H, —COO—$R_3$, —CO—$R_3$, —CO—$N(R_3R_4)$, —$S(O)_2$—$R_3$, —$S(O)_2$—$N(R_3R_4)$, $N(R_3R_4)$, $N(R_4)C(O)R_3$, optionally substituted aryl, or optionally substituted heteroaryl;
$R_2$ is H, D (deuterium), halogen, or optionally substituted alkyl;
each $R_3$ is independently selected from the group consisting of:
(i) H, aryl, substituted aryl, heteroaryl, or substituted heteroaryl;
(ii) heterocycloalkyl or substituted heterocycloalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and
(iv) $NH_2$, $N=CR_4R_6$;
each $R_4$ is independently H, alkyl, alkyl, cycloalkyl, heterocycloalkyl, aryl, or heteroaryl, each of which is optionally substituted;
or $R_3$ and $R_4$ are taken together with the nitrogen atom to which they are attached to form a 4-10-membered ring;
$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;
m is 0, 1, 2, or 3;
provided that
(a) if ring A is thienyl, X is N, R is phenyl or substituted phenyl, $R_2$ is H, RB is methyl, and $R_1$ is —$(CH_2)_n$-L, in which n is 1 and L is —CO—$N(R_3R_4)$, then $R_3$ and $R_4$ are not taken together with the nitrogen atom to which they are attached to form a morpholino ring;
(b) if ring A is thienyl, X is N, R is substituted phenyl, $R_2$ is H, RB is methyl, and $R_1$ is —$(CH_2)$n-L, in which n is 1 and L is —CO—$N(R_3R_4)$, and one of $R_3$ and $R_4$ is H, then the other of $R_3$ and R is not methyl, hydroxyethyl, alkoxy, phenyl, substituted phenyl, pyridyl or substituted pyridyl; and
(c) if ring A is thienyl, X is N, R is substituted phenyl, $R_2$ is H, RB is methyl, and $R_1$ is —$(CH_2)$n-L, in which n is 1 and L is —COO—$R_3$, then $R_3$ is not methyl or ethyl; or a salt, solvate or hydrate thereof.

In certain embodiments, R is aryl or heteroaryl, each of which is optionally substituted.

In certain embodiments, L is H, —COO—$R_3$, —CO—$N(R_3R_4)$, —$S(O)_2$—$R_3$, —$S(O)_2$—$N(R_3R_4)$, $N(R_3R_4)$, $N(R_4)C(O)R_3$ or optionally substituted aryl. In certain embodiments, each $R_3$ is independently selected from the group consisting of: H, —$C_1$-$C_8$ alkyl, containing 0, 1, 2, or 3 heteroatoms selected from O, S, or N; or $NH_2$, $N=CR_4R_6$.

In certain embodiments, $R_1$ is —$(CH_2)_n$-L, in which n is 1 and L is —CO—$N(R_3R_4)$, and one of $R_3$ and $R_4$ is H, and the other of $R_3$ and $R_4$ is $(CH_2)_p$—Y, in which p is 1-3 (e.g., p is 2) and Y is a nitrogen-containing ring (which may be aromatic or non-aromatic).

In certain embodiments, $R_2$ is H, D, halogen or methyl.

In certain embodiments, $R_B$ is alkyl, hydroxyalkyl, haloalkyl, or alkoxy; each of which optionally substituted.

In certain embodiments, $R_B$ is methyl, ethyl, hydroxy methyl, methoxymethyl, trifluoromethyl, COOH, COOMe, COOEt, or $COOCH_2OC(O)CH_3$.

In certain embodiments, ring A is a 5 or 6-membered aryl or heteroaryl. In certain embodiments, ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, ring A is phenyl or thienyl.

In certain embodiments, m is 1 or 2, and at least one occurrence of $R_A$ is methyl.

In certain embodiments, each $R_A$ is independently H, an optionally substituted alkyl, or any two $R_A$ together with the atoms to which each is attached, can form an aryl.

In some aspects, the BET inhibitors is a compound of Formula II:

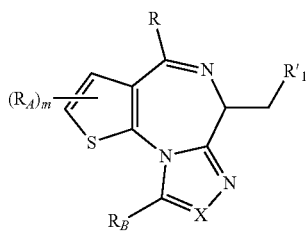

(II)

wherein
X is N or $CR_5$;
$R_5$ is H, alkyl, cycloalkyl, heterocycloalkyl, aryl, or heteroaryl, each of which is optionally substituted;
$R_B$ is H, alkyl, hydroxylalkyl, aminoalkyl, alkoxyalkyl, haloalkyl, hydroxy, alkoxy, or —COO—$R_3$, each of which is optionally substituted;
each RA is independently alkyl, cycloalkyl, heterocycloalkyl, aryl, or heteroaryl, each of which is optionally substituted; or any two RA together with the atoms to which each is attached, can form a fused aryl or heteroaryl group;
R is alkyl, cycloalkyl, heterocycloalkyl, aryl, or heteroaryl, each of which is optionally substituted;
$R'_1$ is H, —COO—$R_3$, —CO—$R_3$, optionally substituted aryl, or optionally substituted heteroaryl;
each $R_3$ is independently selected from the group consisting of:
(i) H, aryl, substituted aryl, heteroaryl, substituted heteroaryl;
(ii) heterocycloalkyl or substituted heterocycloalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl; each of which may be optionally substituted;

m is 0, 1, 2, or 3;
provided that if $R'_1$ is —COO—$R_3$, X is N, R is substituted phenyl, and $R_B$ is methyl, then $R_3$ is not methyl or ethyl;
or a salt, solvate or hydrate thereof.

In certain embodiments, R is aryl or heteroaryl, each of which is optionally substituted. In certain embodiments, R is phenyl or pyridyl, each of which is optionally substituted. In certain embodiments, R is p-Cl-phenyl, o-Cl-phenyl, m-Cl-phenyl, p-F-phenyl, o-F-phenyl, m-F-phenyl or pyridinyl.

In certain embodiments, $R'_1$ is —COO—$R_3$, optionally substituted aryl, or optionally substituted heteroaryl; and $R_3$ is —$C_1$-$C_8$ alkyl, which contains 0, 1, 2, or 3 heteroatoms selected from O, S, or N, and which may be optionally substituted. In certain embodiments, $R'_1$ is —COO—$R_3$, and $R_3$ is methyl, ethyl, propyl, i-propyl, butyl, sec-butyl, or t-butyl; or $R'_1$ is H or optionally substituted phenyl.

In certain embodiments, $R_B$ is methyl, ethyl, hydroxy methyl, methoxymethyl, trifluoromethyl, COOH, COOMe, COOEt, $COOCH_2OC(O)CH_3$.

In certain embodiments, $R_B$ is methyl, ethyl, hydroxy methyl, methoxymethyl, trifluoromethyl, COOH, COOMe, COOEt, or $COOCH_2OC(O)CH_3$. In certain embodiments, each RA is independently an optionally substituted alkyl, or any two RA together with the atoms to which each is attached, can form a fused aryl.

In certain embodiments, each RA is methyl.

In some aspects, the BET inhibitors is a compound of Formula III:

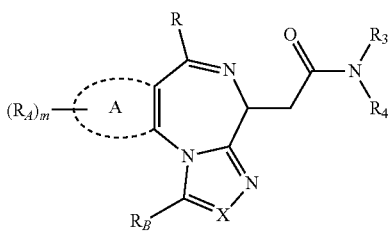

(III)

wherein
X is N or $CR_5$;
$R_5$ is H, alkyl, cycloalkyl, heterocycloalkyl, aryl, or heteroaryl, each of which is optionally substituted;
$R_B$ is H, alkyl, hydroxylalkyl, aminoalkyl, alkoxyalkyl, haloalkyl, hydroxy, alkoxy, or —COO—$R_3$, each of which is optionally substituted;
ring A is aryl or heteroaryl;
each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
R is alkyl, cycloalkyl, heterocycloalkyl, aryl, or heteroaryl, each of which is optionally substituted;
each $R_3$ is independently selected from the group consisting of:
(i) H, aryl, substituted aryl, heteroaryl, or substituted heteroaryl;
(ii) heterocycloalkyl or substituted heterocycloalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and (iv) $NH_2$, $N=CR_4R_6$;

each $R_4$ is independently H, alkyl, alkyl, cycloalkyl, heterocycloalkyl, aryl, or heteroaryl, each of which is optionally substituted;

or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;

provided that:

(a) if ring A is thienyl, X is N, R is phenyl or substituted phenyl, $R_B$ is methyl, then $R_3$ and $R_4$ are not taken together with the nitrogen atom to which they are attached to form a morpholino ring; and (b) if ring A is thienyl, X is N, R is substituted phenyl, $R_2$ is H, $R_B$ is methyl, and one of $R_3$ and $R_4$ is H, then the other of $R_3$ and $R_4$ is not methyl, hydroxyethyl, alkoxy, phenyl, substituted phenyl, pyridyl or substituted pyridyl; and or a salt, solvate or hydrate thereof.

In certain embodiments, R is aryl or heteroaryl, each of which is optionally substituted. In certain embodiments, R is phenyl or pyridyl, each of which is optionally substituted.

In certain embodiments, R is p-Cl-phenyl, o-Cl-phenyl, m-Cl-phenyl, p-F-phenyl, o-F-phenyl, m-F-phenyl or pyridinyl. In certain embodiments, $R_3$ is H, $NH_2$, or $N=CR_4R_6$.

In certain embodiments, each $R_4$ is independently H, alkyl, cycloalkyl, heterocycloalkyl, aryl, heteroaryl; each of which is optionally substituted.

In certain embodiments, is alkyl, alkenyl, cycloalkyl, cycloalkenyl, heterocycloalkyl, aryl, or heteroaryl, each of which is optionally substituted.

In some aspects, the BET inhibitors is a compound of Formula IV:

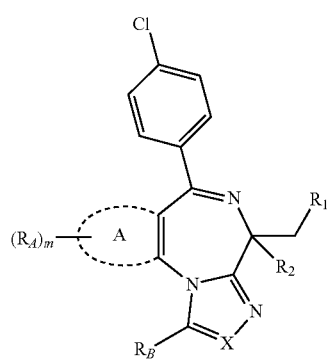

(IV)

wherein

X is N or $CR_5$;

$R_5$ is H, alkyl, cycloalkyl, heterocycloalkyl, aryl, or heteroaryl, each of which is optionally substituted;

$R_B$ is H, alkyl, hydroxylalkyl, aminoalkyl, alkoxyalkyl, haloalkyl, hydroxy, alkoxy, or —COO—$R_3$, each of which is optionally substituted;

ring A is aryl or heteroaryl;

each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;

$R_1$ is —$(CH_2)_n$-L, in which n is 0-3 and L is H, —COO—$R_3$, —CO—$R_3$, —CO-N($R_3R_4$), —S(O)$_2$—$R_3$, —S(O)$_2$—N($R_3R_4$), N($R_3R_4$), N($R_4$)C(O)$R_3$, optionally substituted aryl, or optionally substituted heteroaryl;

$R_2$ is H, D, halogen, or optionally substituted alkyl;

each $R_3$ is independently selected from the group consisting of:

(i) H, aryl, substituted aryl, heteroaryl, or substituted heteroaryl;

(ii) heterocycloalkyl or substituted heterocycloalkyl;

(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and (iv) $NH_2$, $N=CR_4R_6$;

each $R_4$ is independently H, alkyl, alkyl, cycloalkyl, heterocycloalkyl, aryl, or heteroaryl, each of which is optionally substituted;

or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;

provided that (a) if ring A is thienyl, X is N, $R_2$ is H, RB is methyl, and $R_1$ is —$(CH_2)_n$-L, in which n is 0 and L is is —CO—N(Ra$R_4$), then $R_3$ and $R_4$ are not taken together with the nitrogen atom to which they are attached to form a morpholino ring;

(b) if ring A is thienyl, X is N, $R_2$ is H, RB is methyl, and $R_1$ is —$(CH_2)_n$-L, in which n is 0 and L is —CO—N($R_3R_4$), and one of $R_3$ and $R_4$ is H, then the other of $R_3$ and $R_4$ is not methyl, hydroxyethyl, alkoxy, phenyl, substituted phenyl, pyridyl or substituted pyridyl; and (c) if ring A is thienyl, X is N, $R_2$ is H, RB is methyl, and $R_1$ is —$(CH_2)_n$-L, in which n is 0 and L is —COO—$R_3$, then $R_3$ is not methyl or ethyl; or a salt, solvate or hydrate thereof.

In certain embodiments, $R_1$ is —$(CH_2)_n$-L, in which n is 0-3 and L is —COO—$R_3$, optionally substituted aryl, or optionally substituted heteroaryl; and $R_3$ is —$C_1$-$C_8$ alkyl, which contains 0, 1, 2, or 3 heteroatoms selected from O, S, or N, and which may be optionally substituted. In certain embodiments, n is 1 or 2 and L is alkyl or —COO—$R_3$, and $R_3$ is methyl, ethyl, propyl, i-propyl, butyl, sec-butyl, or t-butyl; or n is 1 or 2 and L is H or optionally substituted phenyl.

In certain embodiments, $R_2$ is H or methyl.

In certain embodiments, $R_B$ is methyl, ethyl, hydroxy methyl, methoxymethyl, trifluoromethyl, COOH, COOMe, COOEt, COOCH2OC(O)CH$_3$.

In certain embodiments, ring A is phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, each R$_A$ is independently an optionally substituted alkyl, or any two R$_A$ together with the atoms to which each is attached, can form an aryl.

The methods of the invention also relate to compounds of Formulae V-XXII, and to any compound described herein.

In another aspect, the compound is a compound represented by the formula:

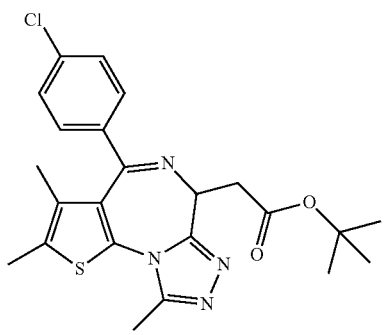 [SMILES: Cc1sc2c(c1C)C(c1ccc(Cl)cc1)=NC(CC(=O)OC(C)(C)C)c1nnc(C)n1-2]

or a salt, solvate or hydrate thereof.

In certain embodiments, the compound is (+)-JQ1:

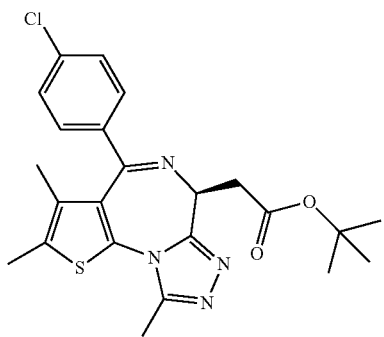 [SMILES: Cc1sc2c(c1C)C(c1ccc(Cl)cc1)=N[C@@H](CC(=O)OC(C)(C)C)c1nnc(C)n1-2]

or a salt, solvate or hydrate thereof.

In another aspect, the compound is a compound represented by the formula:

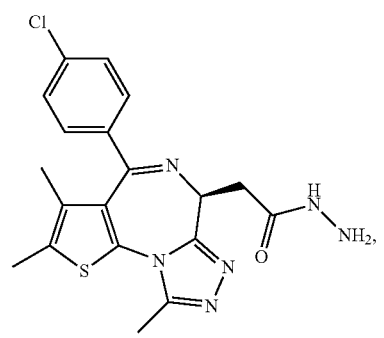

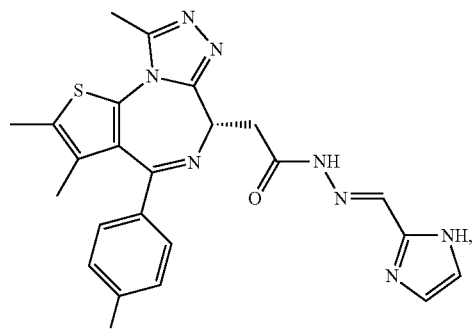

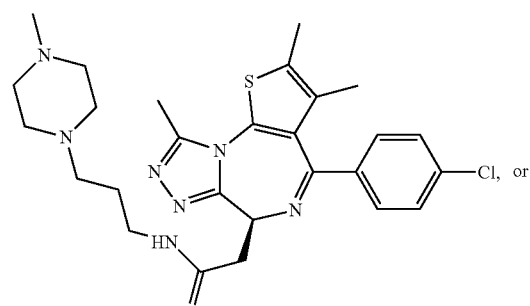

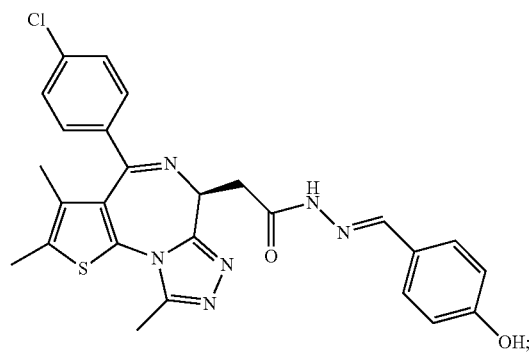

or a salt, solvate or hydrate thereof.

In another aspect, the compound is a compound represented by the formula:
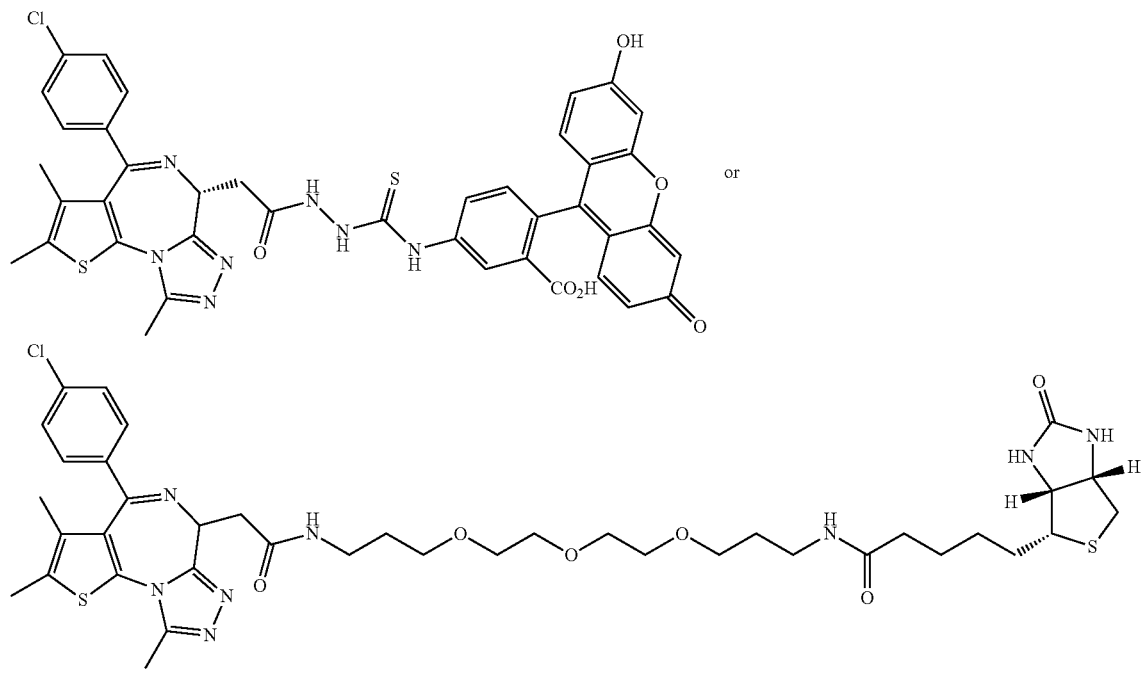
or a salt, solvate or hydrate thereof.
In another aspect, the compound is a compound represented by any one of the following formulae:
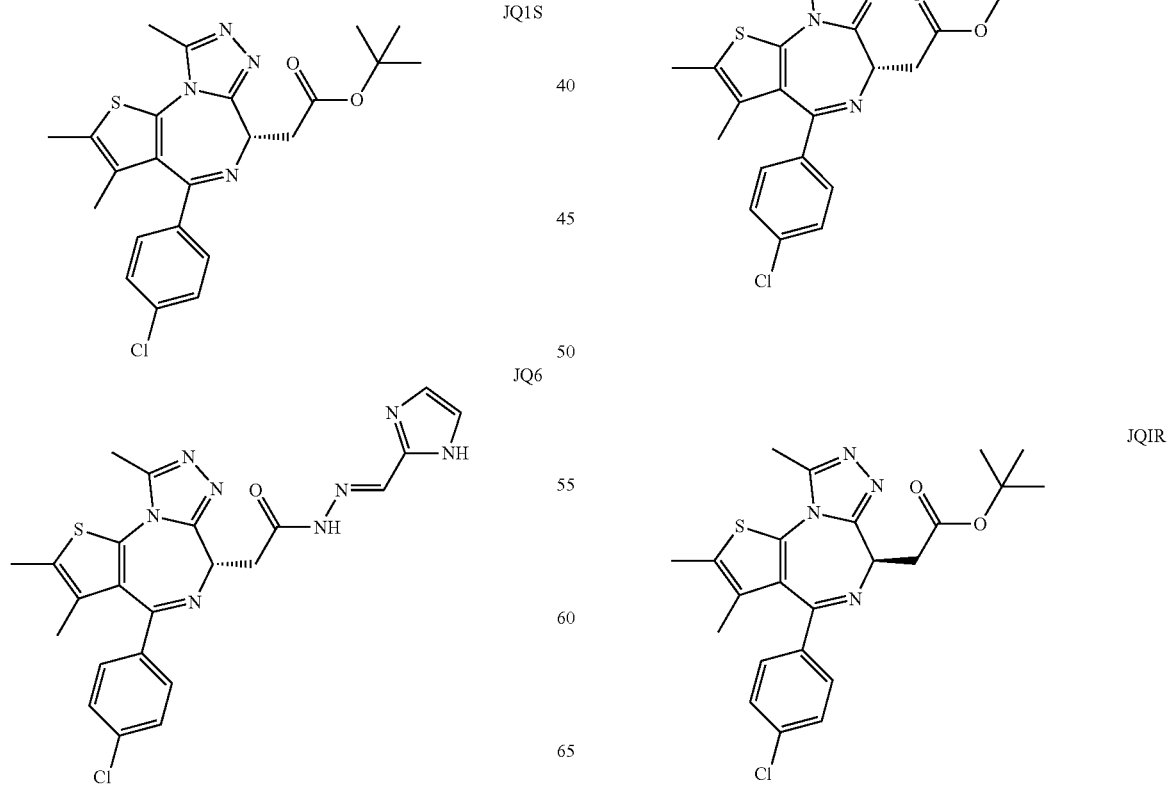

-continued
JQ13
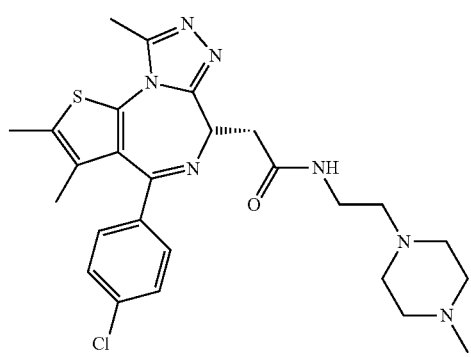
JQ21
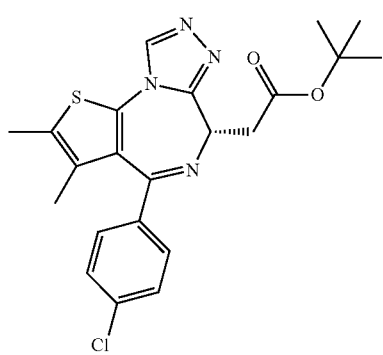
JQ20
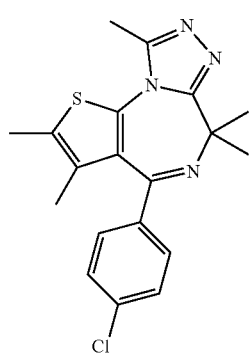
JQ19
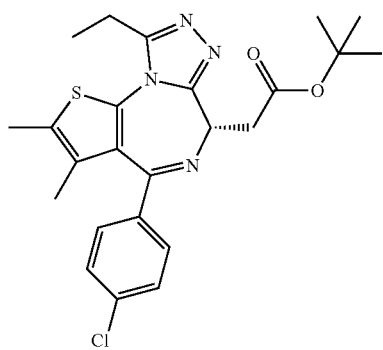
-continued
JQ24B
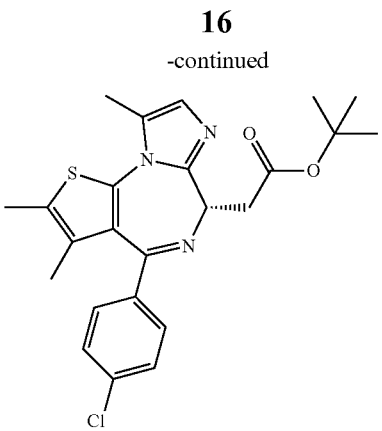
JQ8
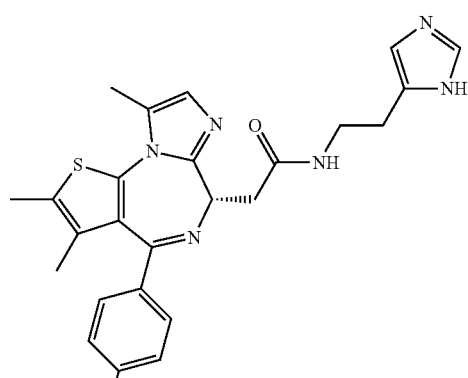
JQ18
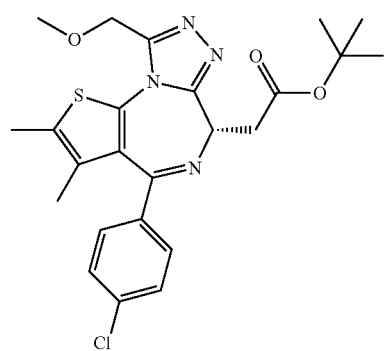
KS1
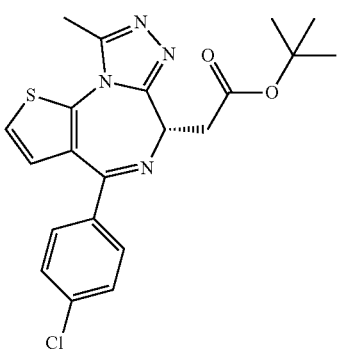
or a salt, solvate or hydrate thereof.

In another aspect, the compound is a compound represented by any one of the following formulae:
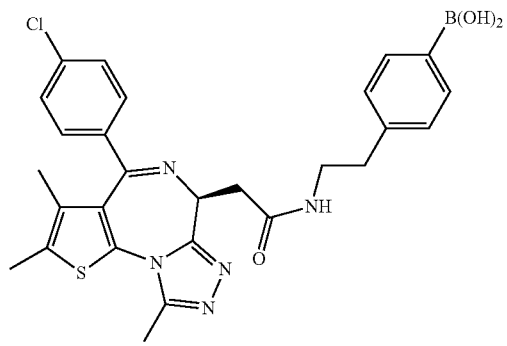
or
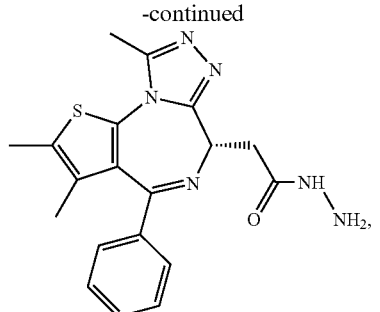
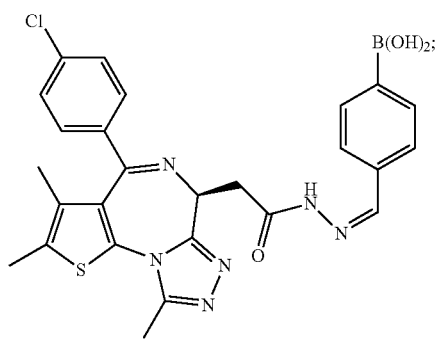
or a salt, solvate or hydrate thereof.
In another aspect, the compound is a compound represented by any one of the following:
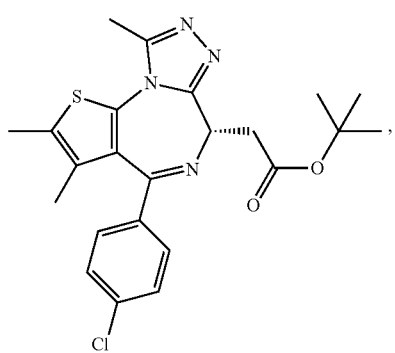
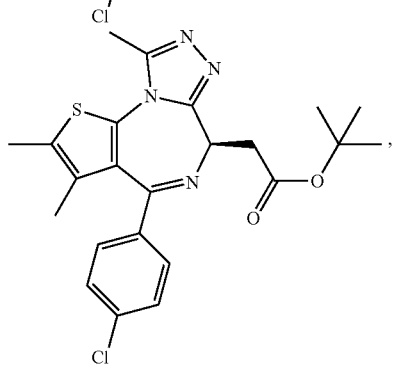
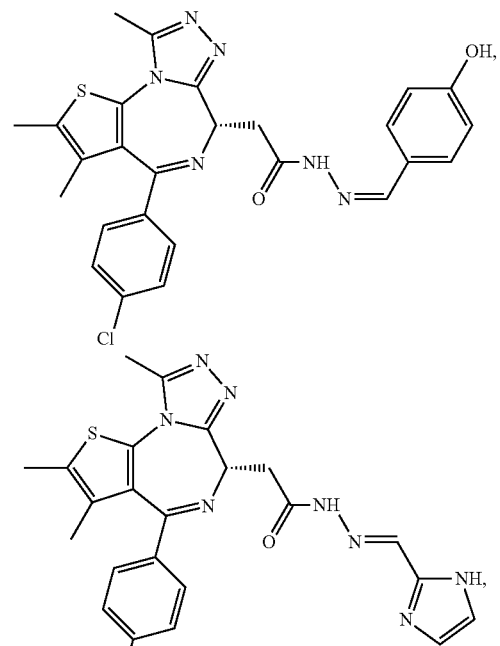
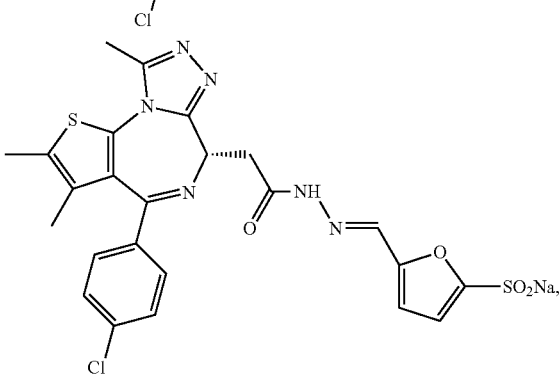
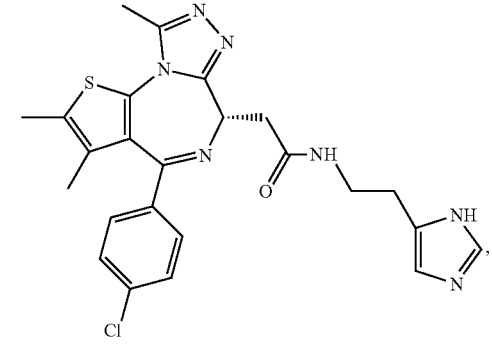

19
-continued
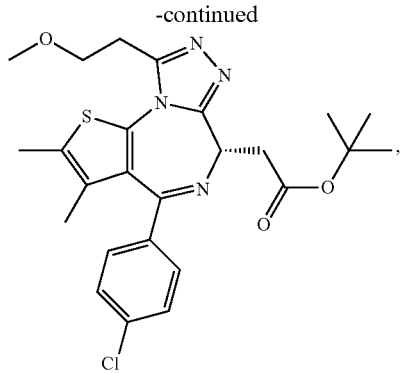
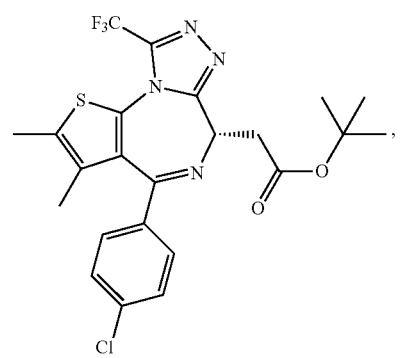
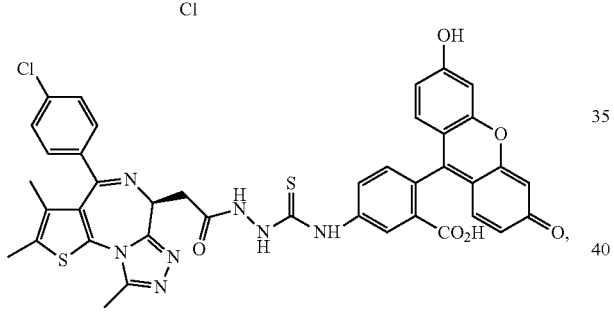
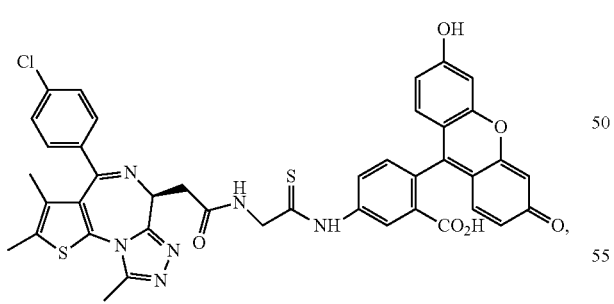
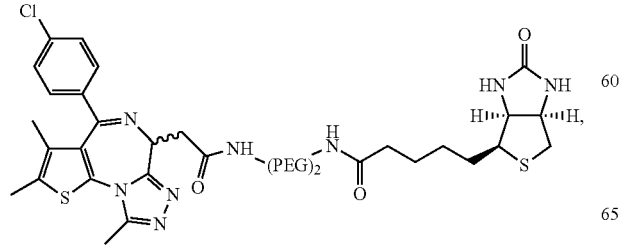
20
-continued
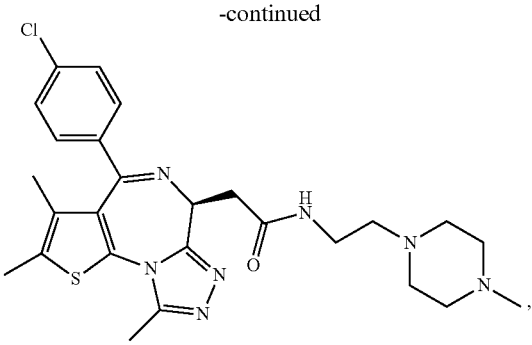
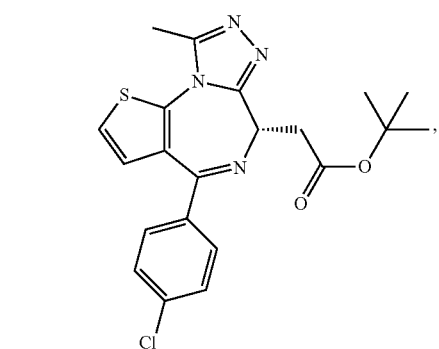
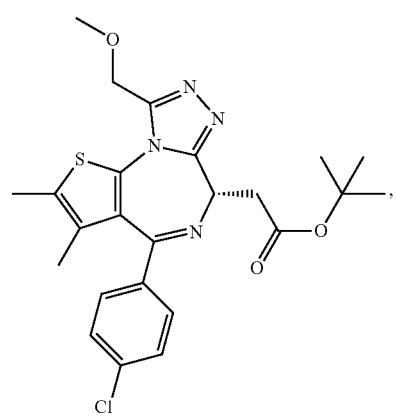
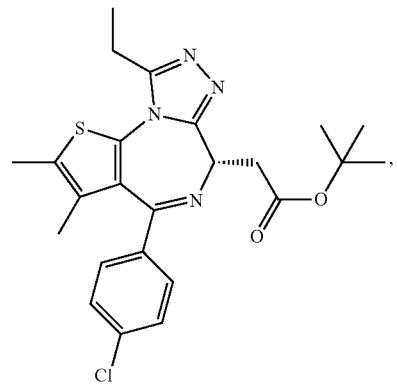

-continued
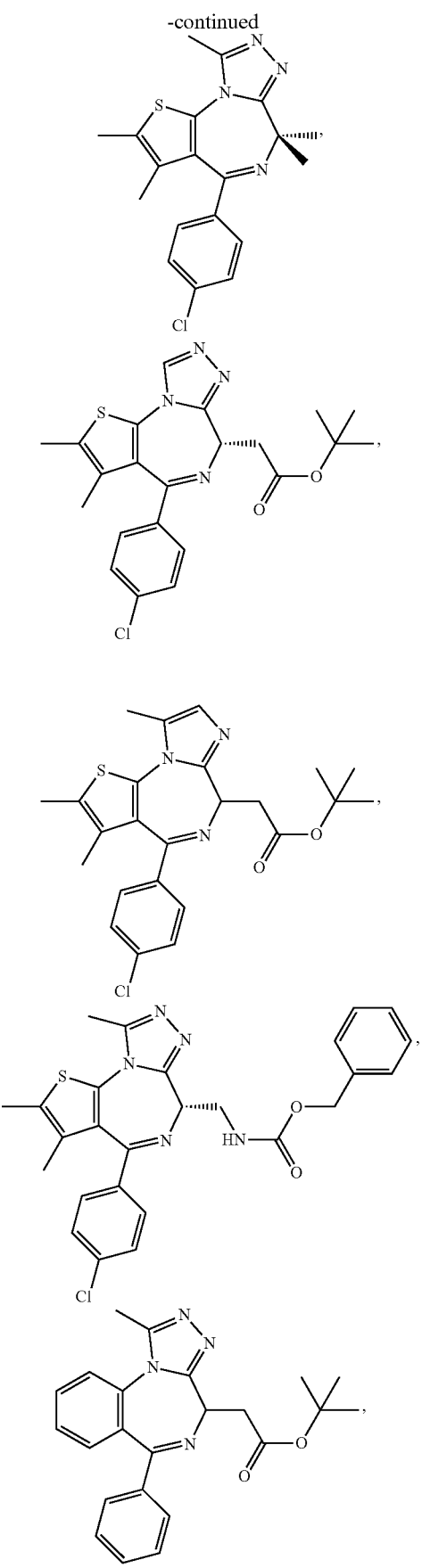
-continued
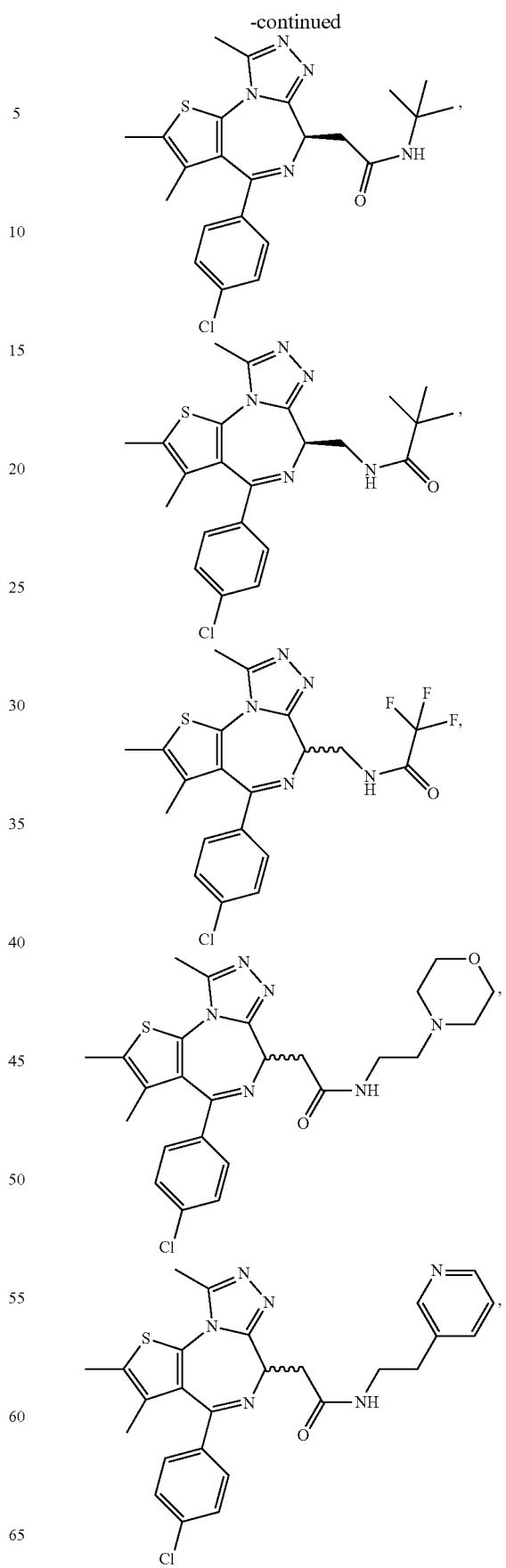

23
-continued
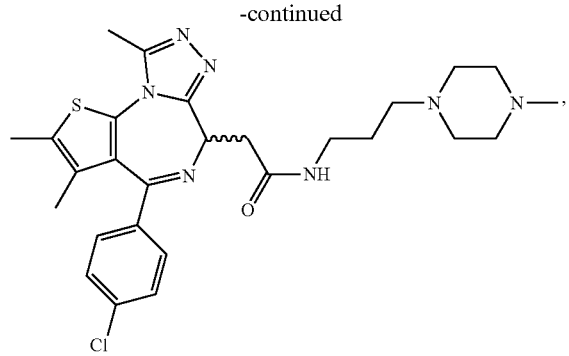
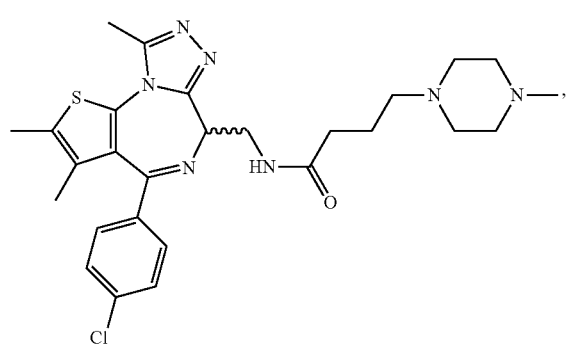
24
-continued
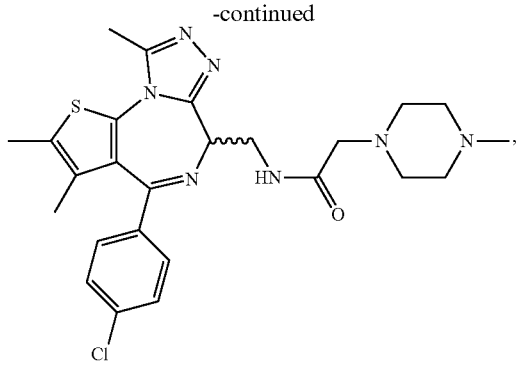
or a salt, solvate or hydrate thereof.
In certain embodiments, a compound of the invention can be represented by one of the following structures:
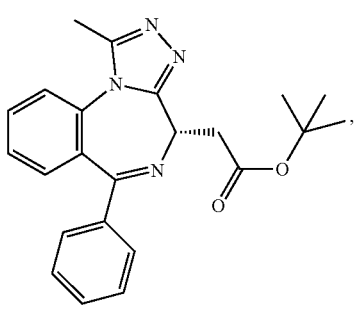
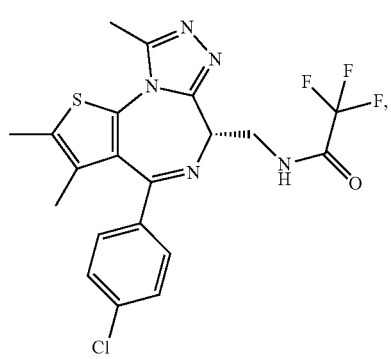

-continued
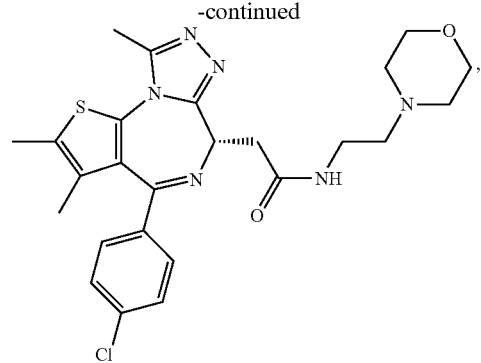
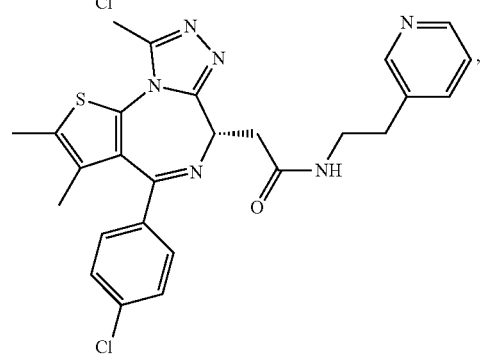
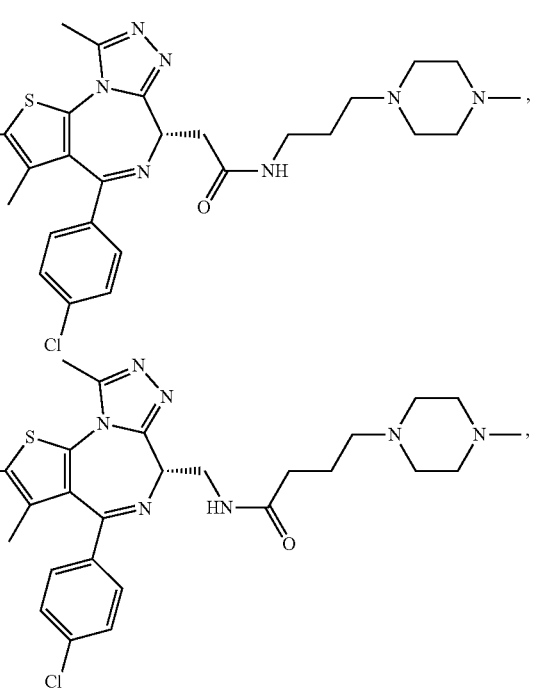
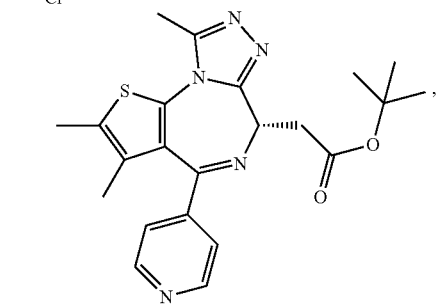
-continued
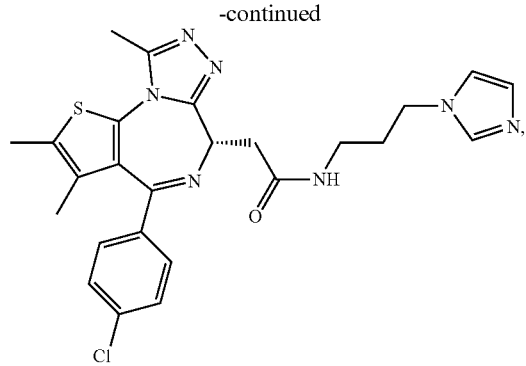
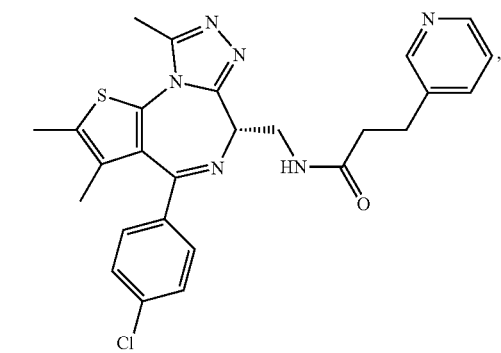
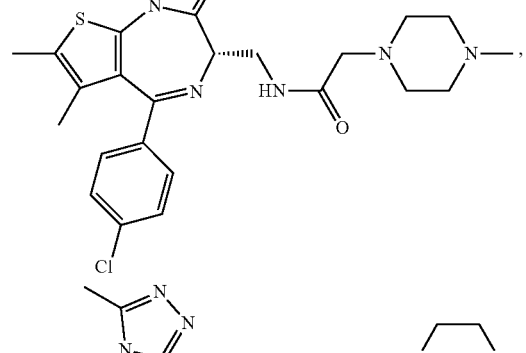
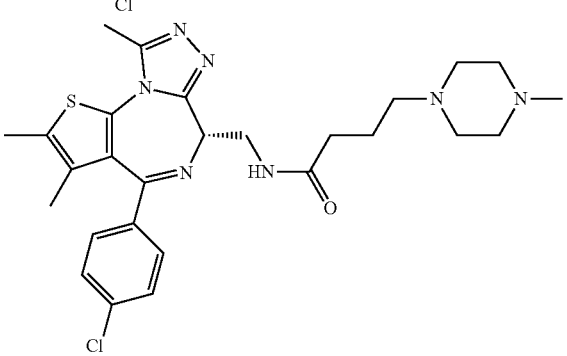
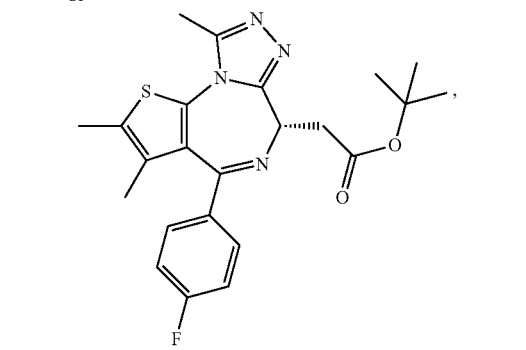

27
-continued
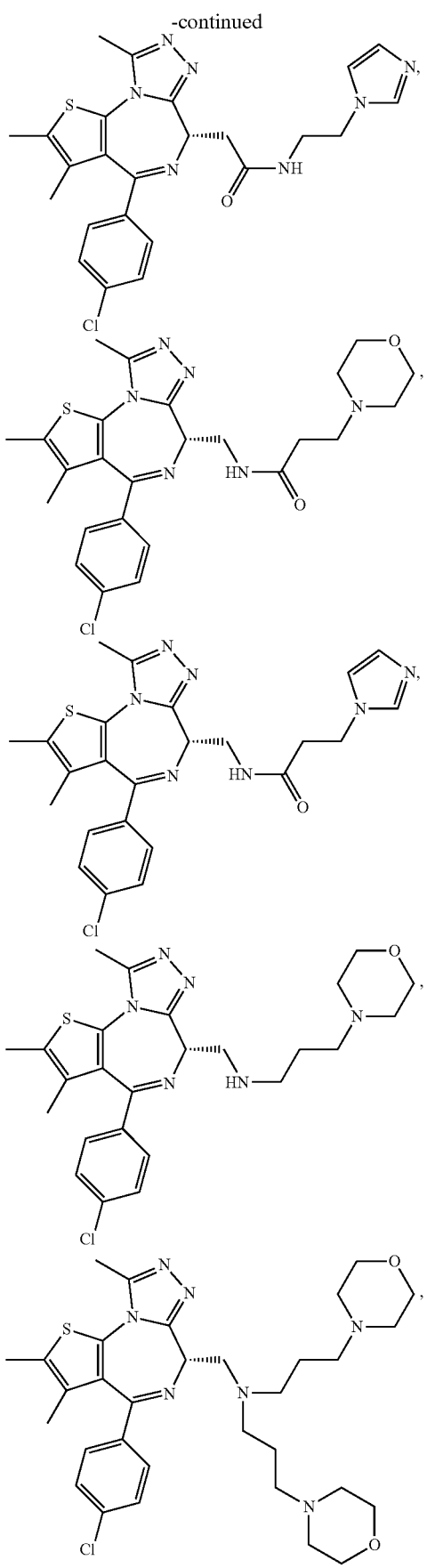
28
-continued
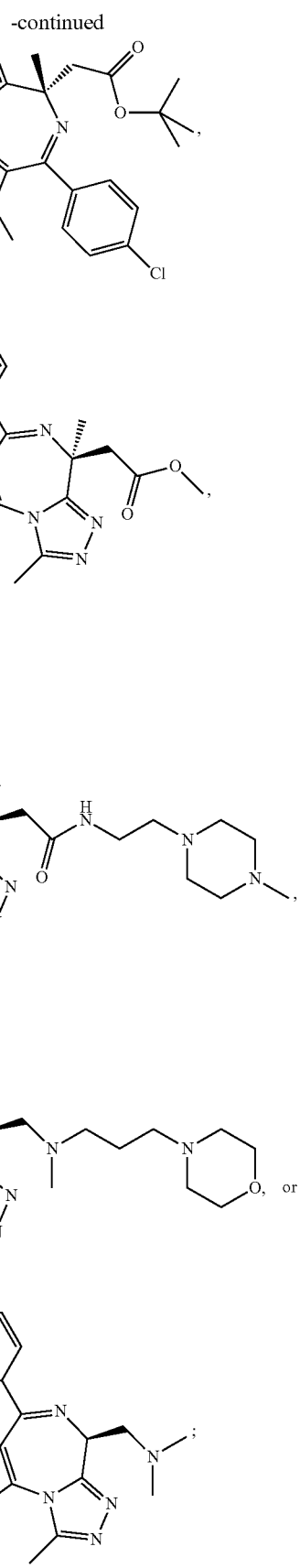
or a salt, solvate or hydrate thereof.

In one embodiment, the compound is represented by the structure:

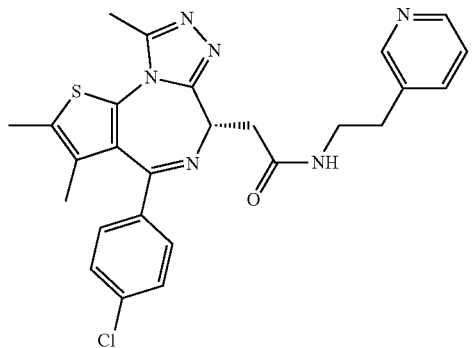 [SMILES: Cc1sc2c(c1C)C(c1ccc(Cl)cc1)=N[C@@H](CC(=O)NCCc1cccnc1)c1nnc(C)n1-2]

or a salt, solvate or hydrate thereof. In another embodiment, the compound is represented by the structure:

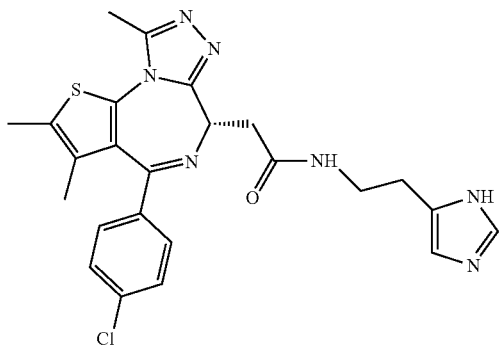 [SMILES: Cc1sc2c(c1C)C(c1ccc(Cl)cc1)=N[C@@H](CC(=O)NCCc1cnc[nH]1)c1nnc(C)n1-2]

or a salt, solvate or hydrate thereof.

In another embodiment, the compound is represented by the structure:

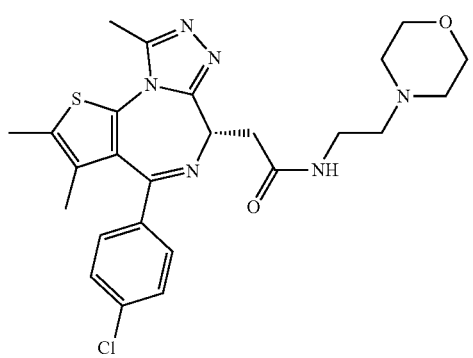 [SMILES: Cc1sc2c(c1C)C(c1ccc(Cl)cc1)=N[C@@H](CC(=O)NCCN1CCOCC1)c1nnc(C)n1-2]

or a salt, solvate or hydrate thereof.

In certain embodiments, a compound of the invention can have the opposite chirality of any compound shown herein.

In certain embodiments, the compound is a compound represented by Formula (V), (VI), or (VII):

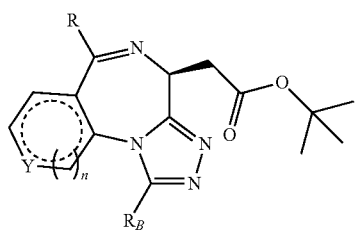

(V)

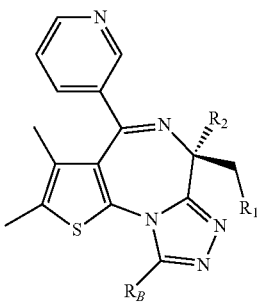

(VI)

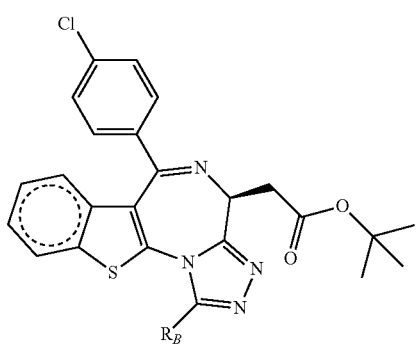

(VII)

in which R, $R_1$ and $R_2$ and $R_B$ have the same meaning as in Formula (I); Y is O, N, S, or $CR_5$, in which $R_5$ has the same meaning as in Formula (I); n is 0 or 1; and the dashed circle in Formula (VII) indicates an aromatic or non-aromatic ring; or a salt, solvate, or hydrate thereof.

In certain embodiments of any of the Formulae I- IV and VI (or any formula herein), $R_6$ represents the non-carbonyl portion of an aldehyde shown in the tables below (i.e., for an aldehyde of formula $R_6CHO$, $R_6$ is the non-carbonyl portion of the aldehyde). In certain embodiments, $R_4$ and $R_6$ together represent the non-carbonyl portion of a ketone shown below (i.e., for a ketone of formula $R_6C(O)R_4$, $R_4$ and $R_6$ are the non-carbonyl portion of the ketone).

TABLE A

| | Plate 1 | | |
|---|---|---|---|
| | 01 | 02 | 03 |
| A | | (OH, F-substituted benzaldehyde) | (imidazole carbaldehyde) |

TABLE A-continued
| | | | |
|---|---|---|---|
| B | 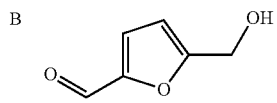 | 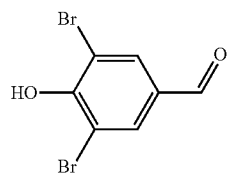 [SMILES: O=Cc1cc(Br)c(O)c(Br)c1] | 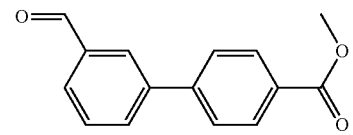 [SMILES: COC(=O)c1ccc(-c2cccc(C=O)c2)cc1] |
| C | 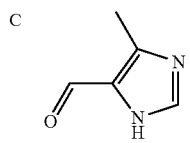 | 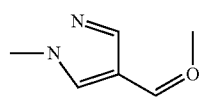 | 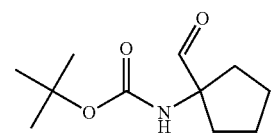 |
| D | 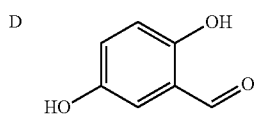 | 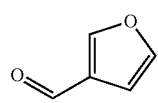 | 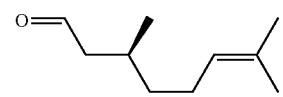 |
| E | 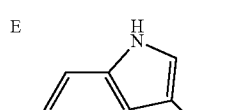 | 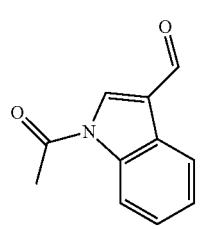 | |
| F | 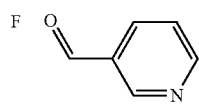 | 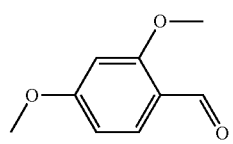 | 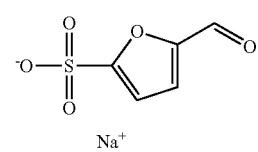 |
| G | 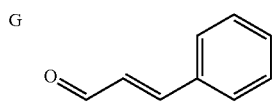 | 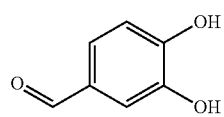 | 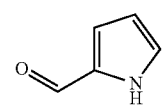 |
| H | 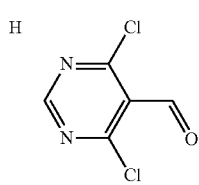 | 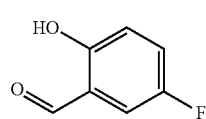 | 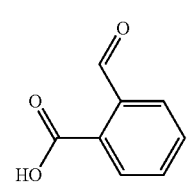 [SMILES: O=Cc1ccccc1C(=O)O] |
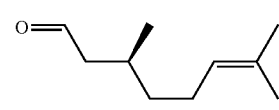
Plate 2
| | 01 | 02 | 03 |
|---|---|---|---|
| A | | 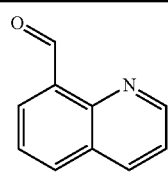 | 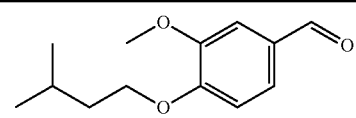 |
| B | | 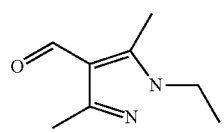 | 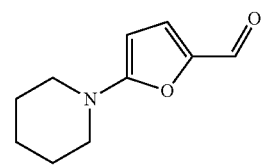 [SMILES: O=Cc1ccc(N2CCCCC2)o1] |

TABLE A-continued
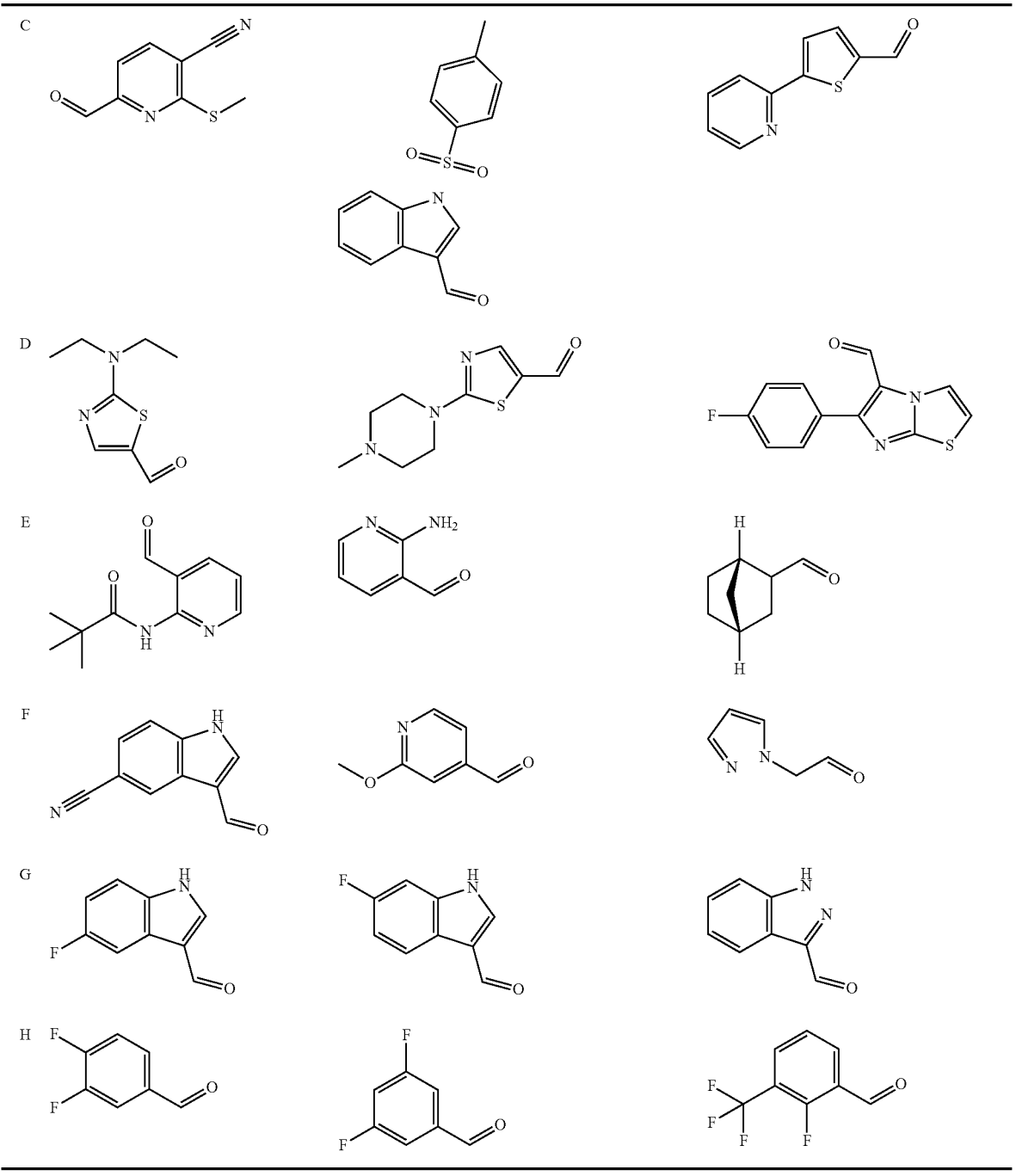
| | Plate 3 | |
|---|---|---|
| 01 | 02 | 03 |
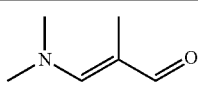
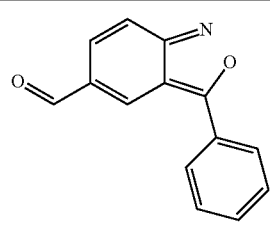

TABLE A-continued
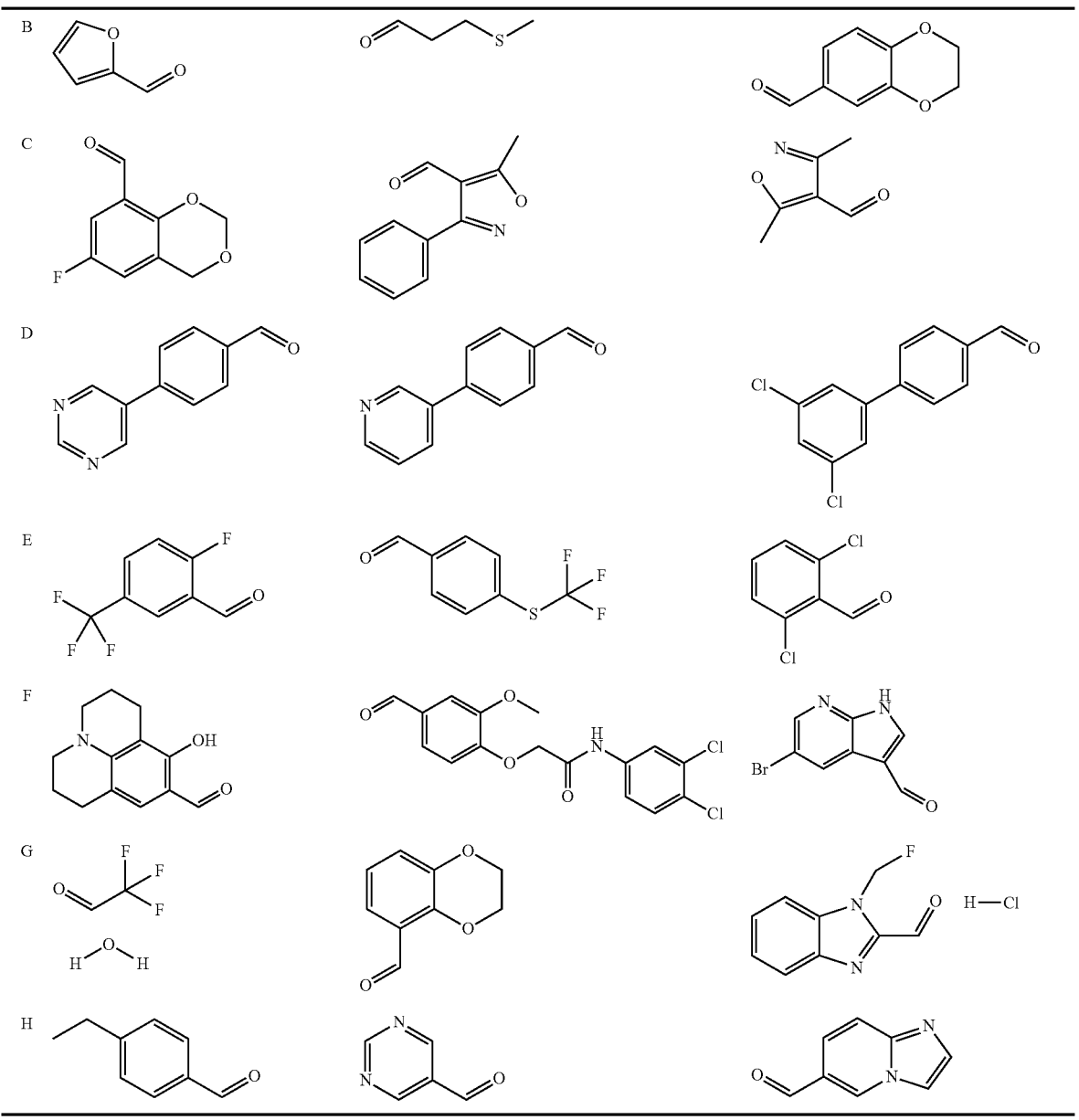
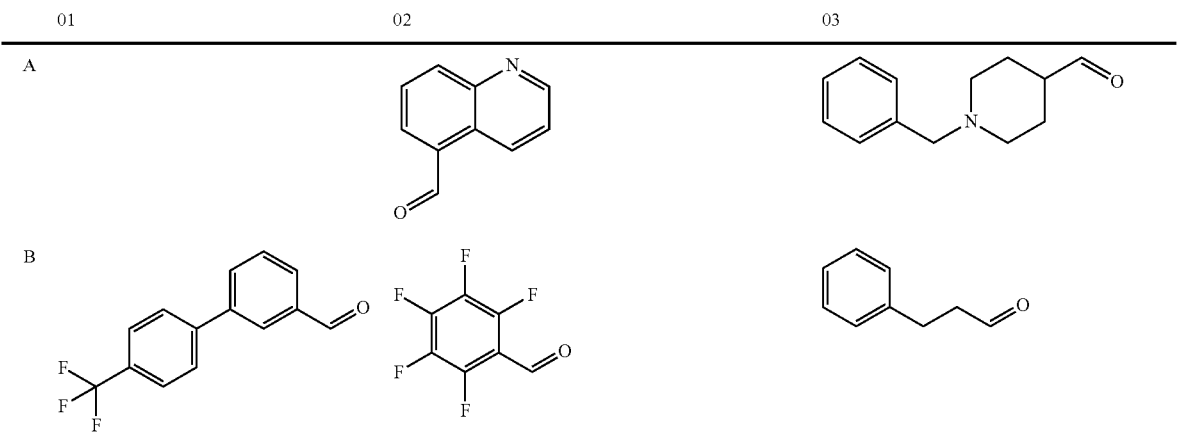

TABLE A-continued
| | | | |
|---|---|---|---|
| C | 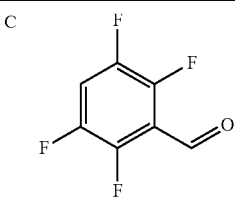 | 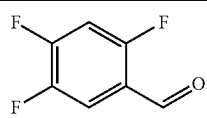 | 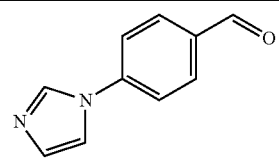 |
| D | 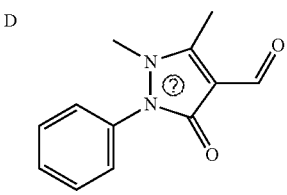 | 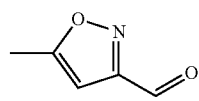 | 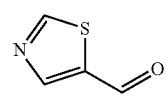 |
| E | 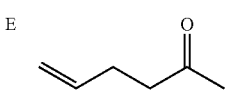 | 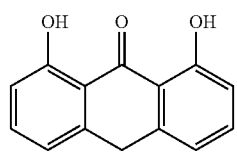 [SMILES: O=C1c2c(O)cccc2Cc2cccc(O)c21] | 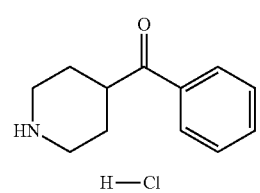 |
| F | 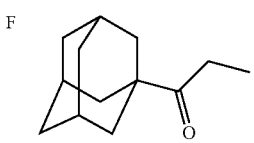 | 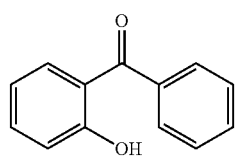 [SMILES: O=C(c1ccccc1)c1ccccc1O] | 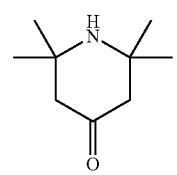 |
| G | 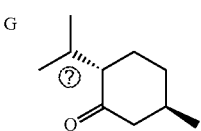 | 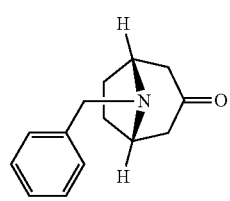 [SMILES: O=C1C[C@H]2CC[C@@H](C1)N2Cc1ccccc1] | 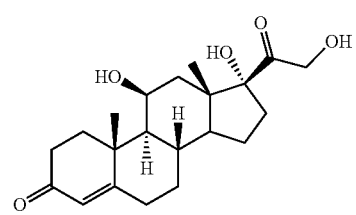 |
| H | | | |
Plate 1
| | 04 | 05 | 06 |
|---|---|---|---|
| A | 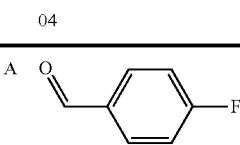 | 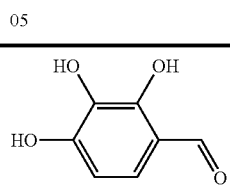 | 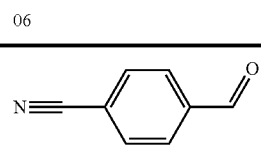 |
| B | 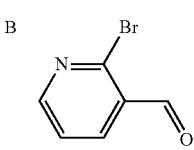 | 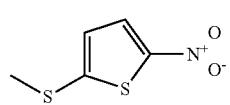 | 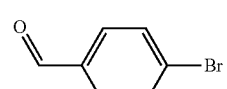 |
| C | 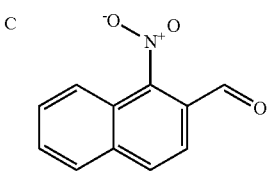 | | 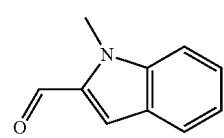 |

US 10,813,939 B2
TABLE A-continued
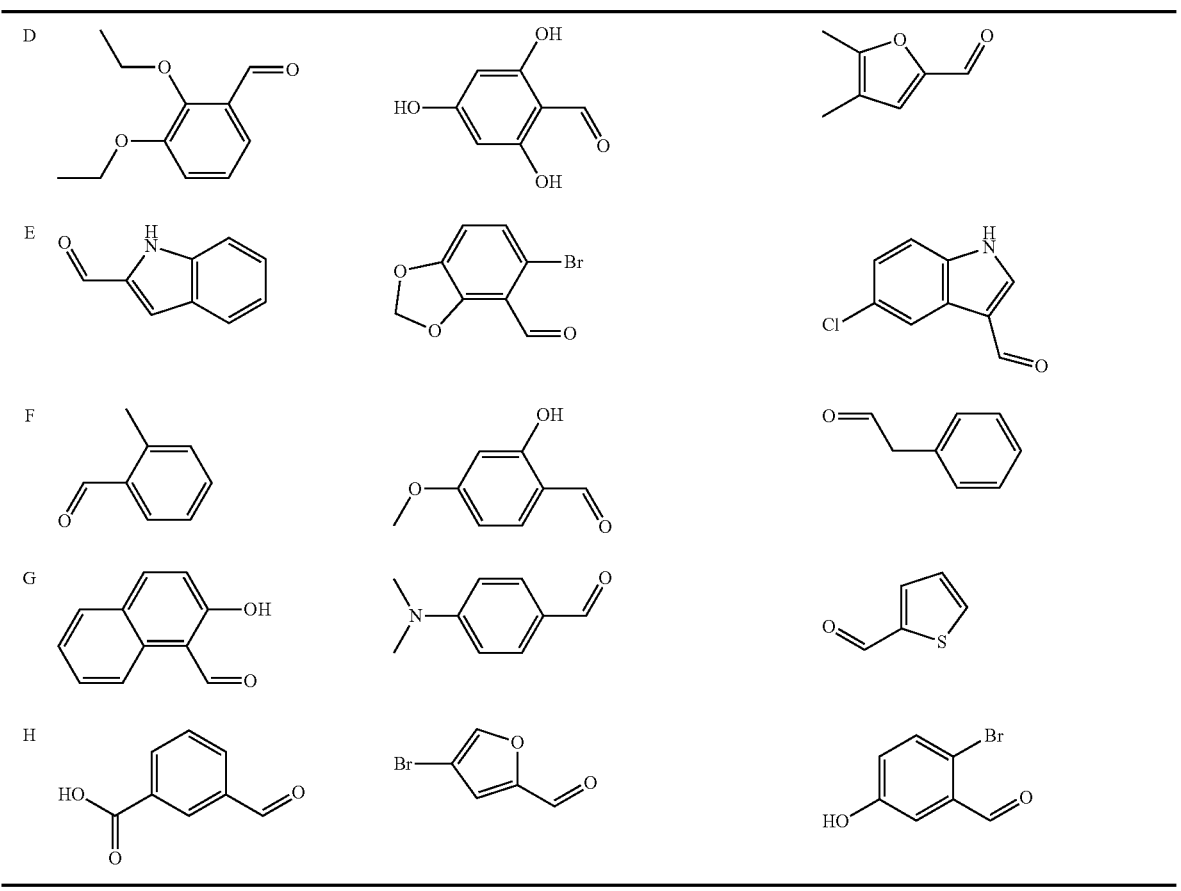
| | Plate 2 | | |
|---|---|---|---|
| | 04 | 05 | 06 |
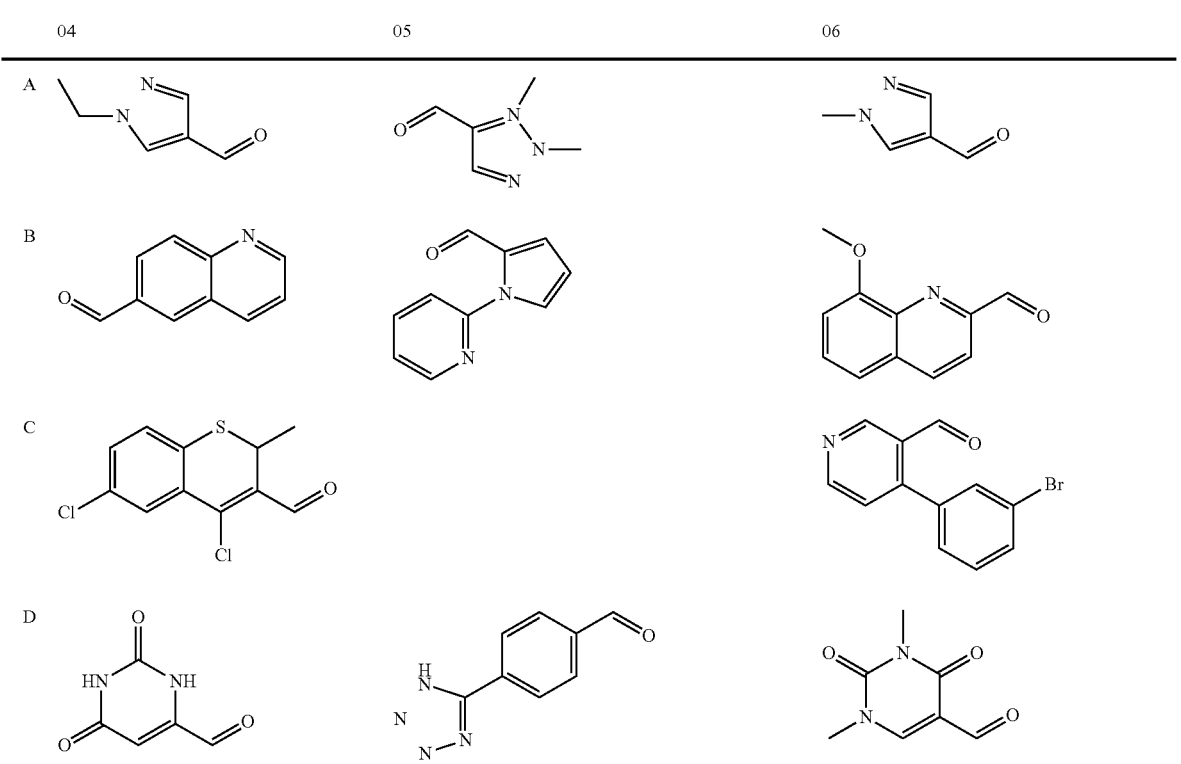

TABLE A-continued
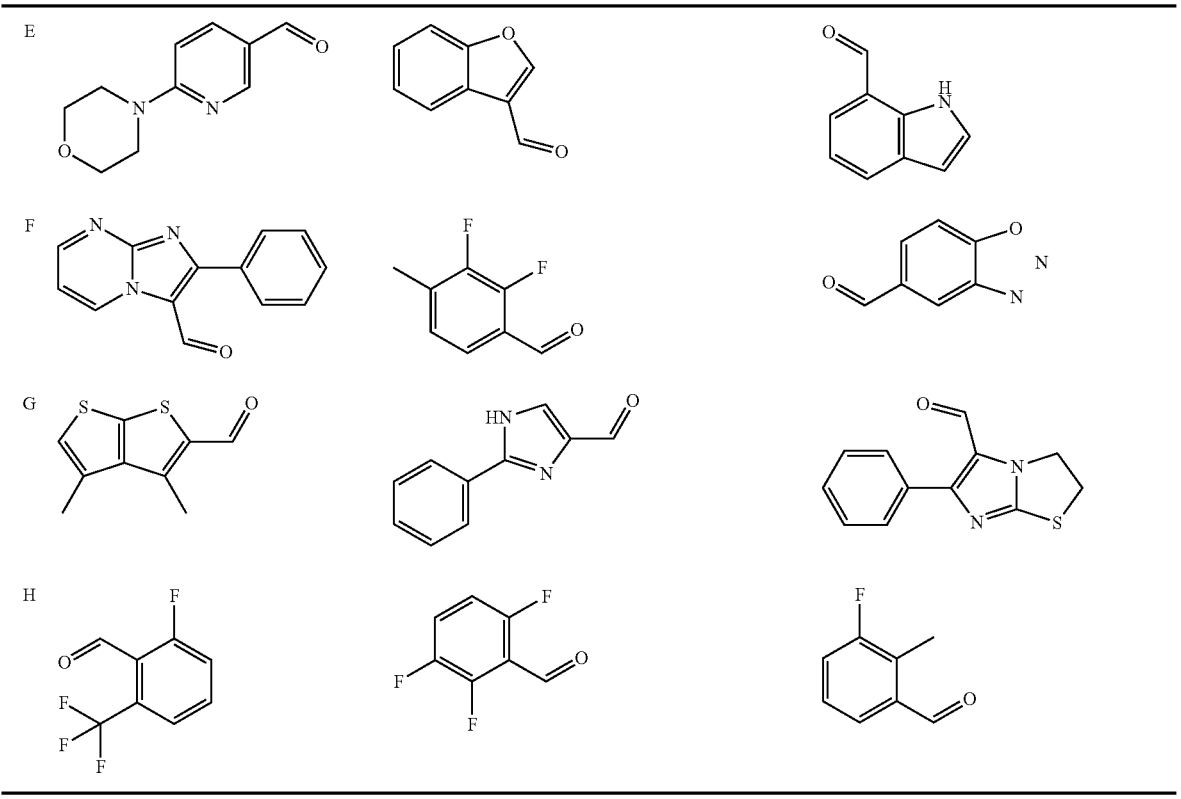
| | 04 | 05 | 06 |
|---|---|---|---|
Plate 3
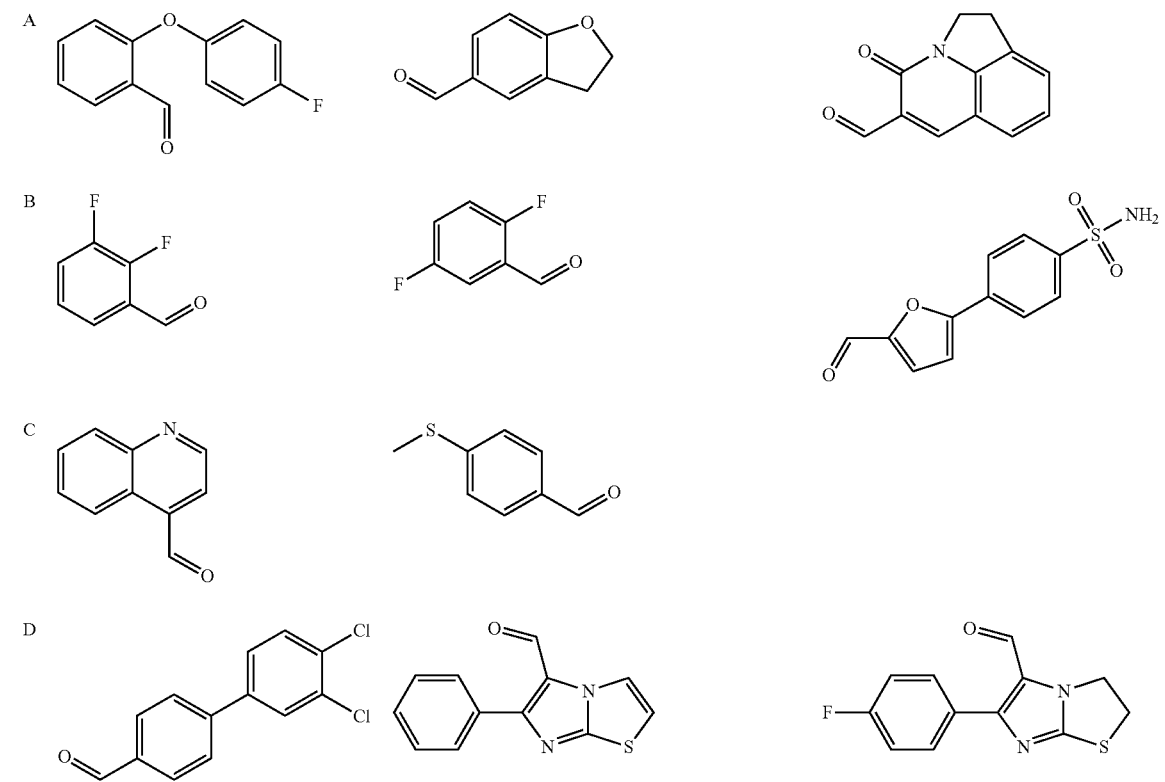

TABLE A-continued
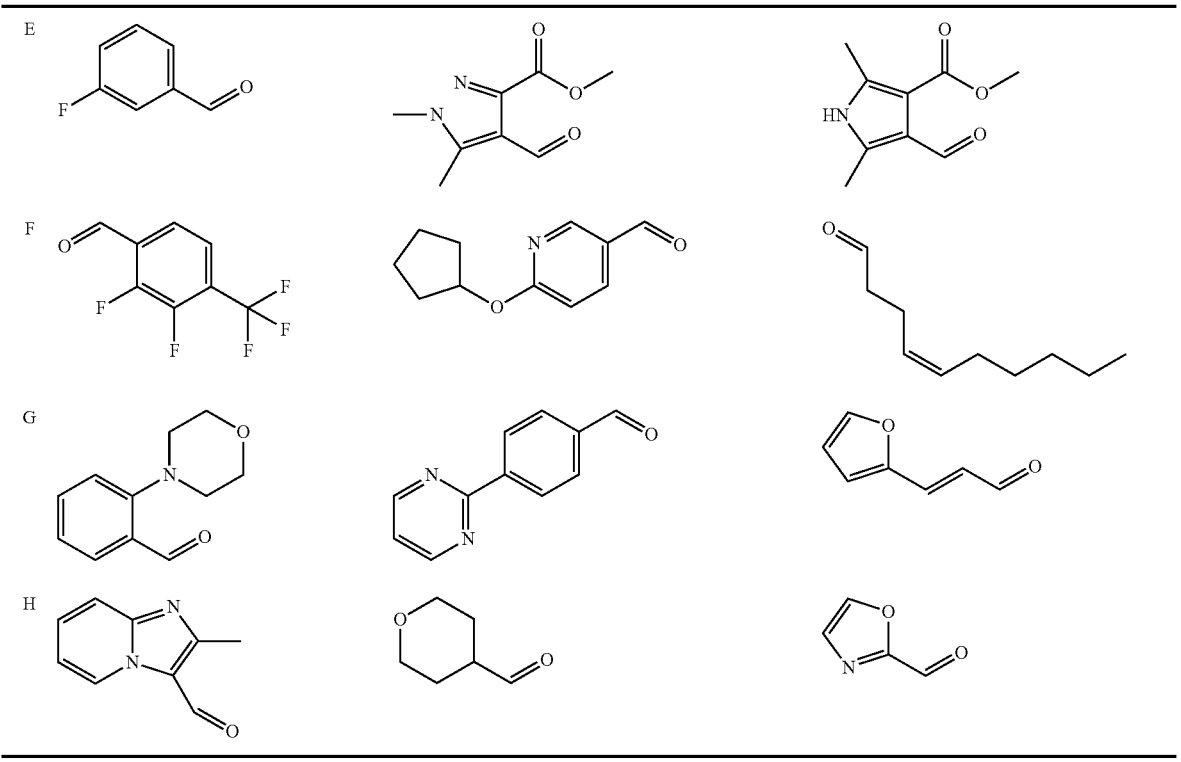
| | Plate 4 | |
|---|---|---|
| 04 | 05 | 06 |
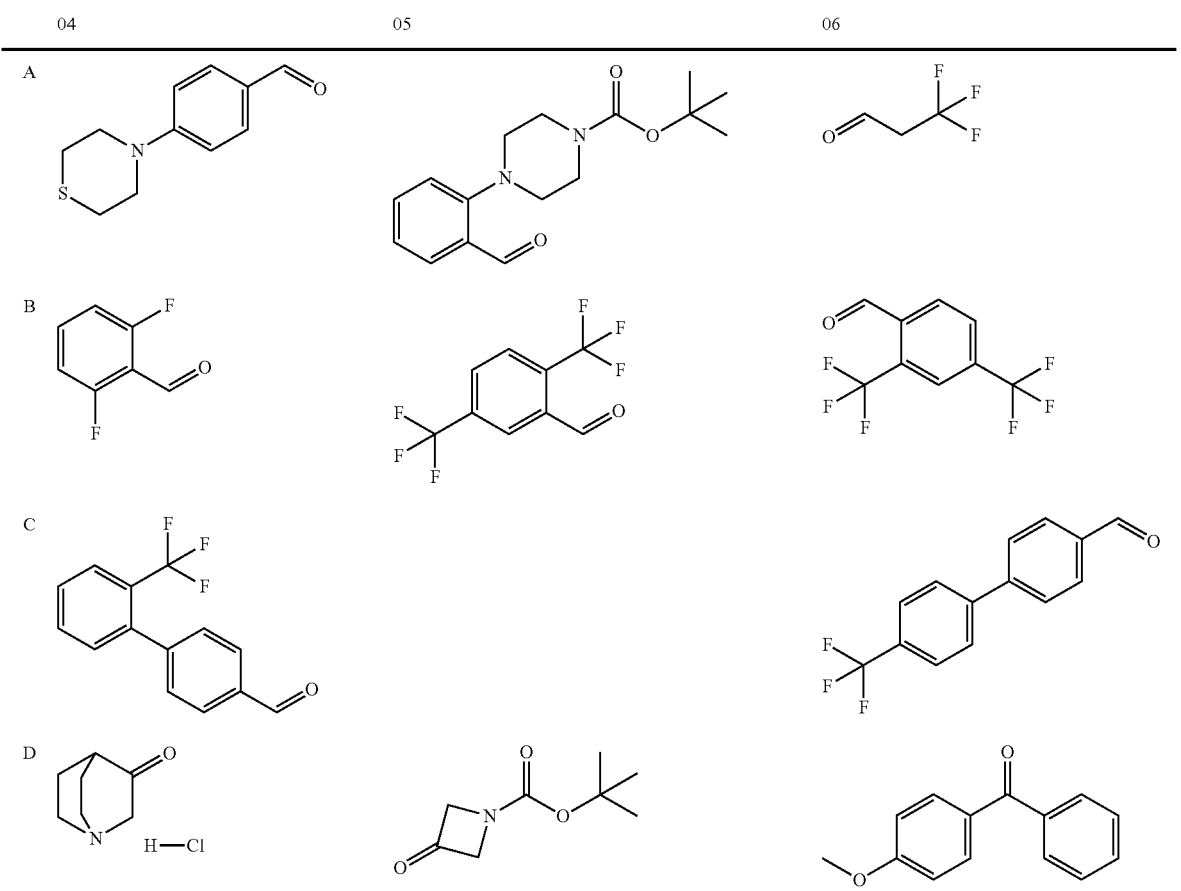

TABLE A-continued
| | | | |
|---|---|---|---|
| E | 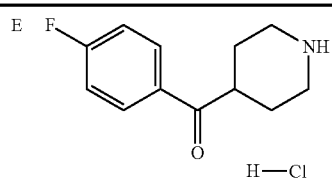 | 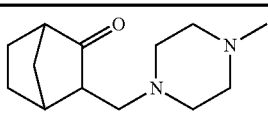 | 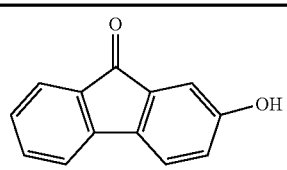 |
| F | 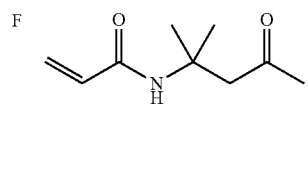 | 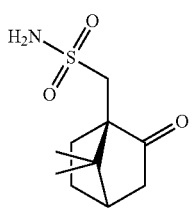 | 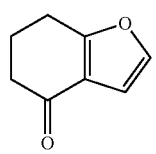 |
| G | 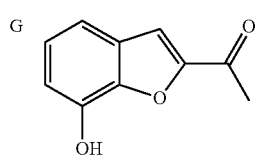 | 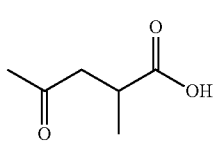 | 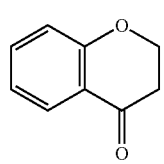 [SMILES: O=C1CCOc2ccccc21] |
| H | | | |
| Plate 1 | | |
|---|---|---|
| 07 | 08 | 09 |
| | 07 | 08 | 09 |
|---|---|---|---|
| A | 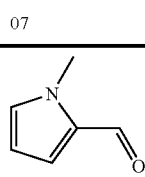 | 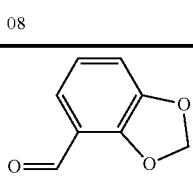 | 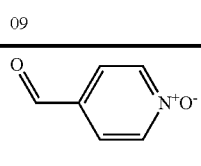 |
| B | 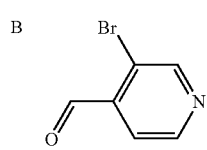 | 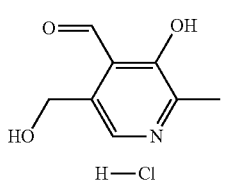 | 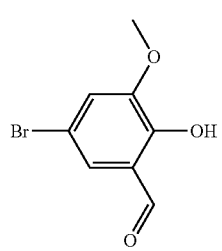 |
| C | 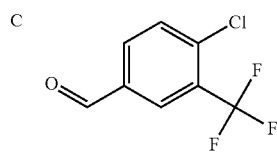 | 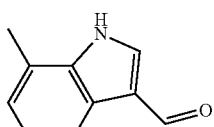 | 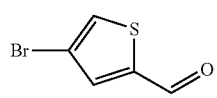 |
| D | 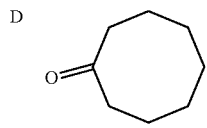 | 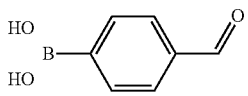 | |
| E | 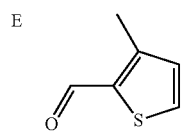 | 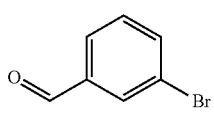 | <br>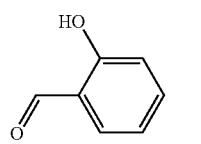 |
| F | 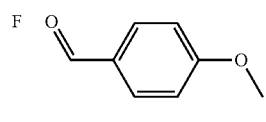 | 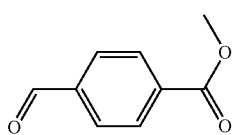 | 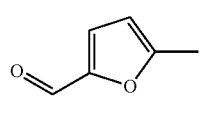 |

TABLE A-continued
| | 07 | 08 | 09 |
|---|---|---|---|
| G | | 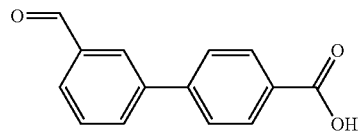 | 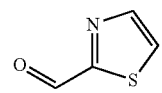 |
| H | 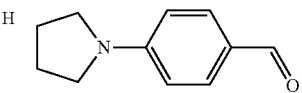 | 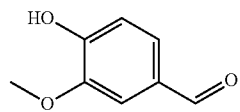 | 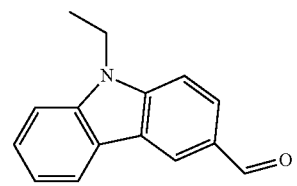 [SMILES: CCn1c2ccccc2c2cc(C=O)ccc21] |
Plate 2
| | 07 | 08 | 09 |
|---|---|---|---|
| A | 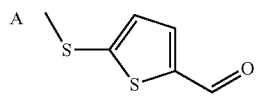 | 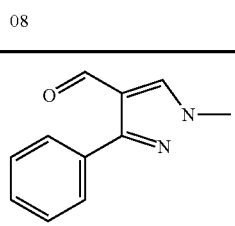 | 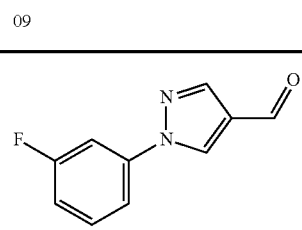 |
| B | 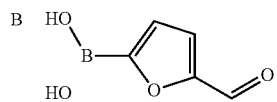 | 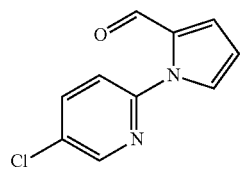 [SMILES: O=Cc1cccn1-c1ccc(Cl)cn1] | 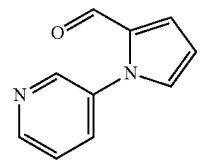 [SMILES: O=Cc1cccn1-c1cccnc1] |
| C | 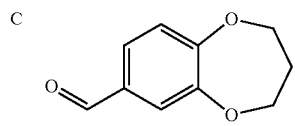 | 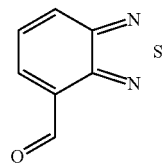 | 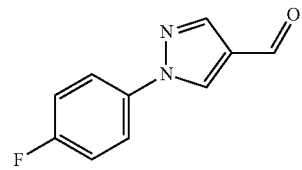 |
| D | 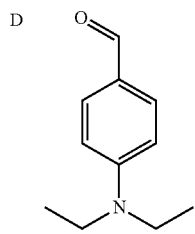 | 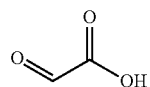 | |
| E | 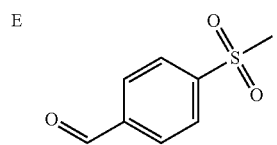 | 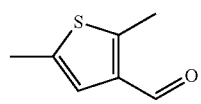 | 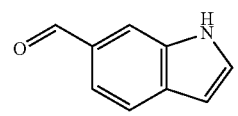 [SMILES: O=Cc1ccc2cc[nH]c2c1] |
| F | 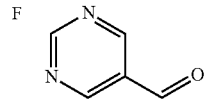 | 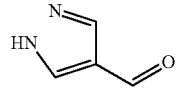 | 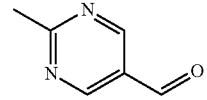 |

TABLE A-continued
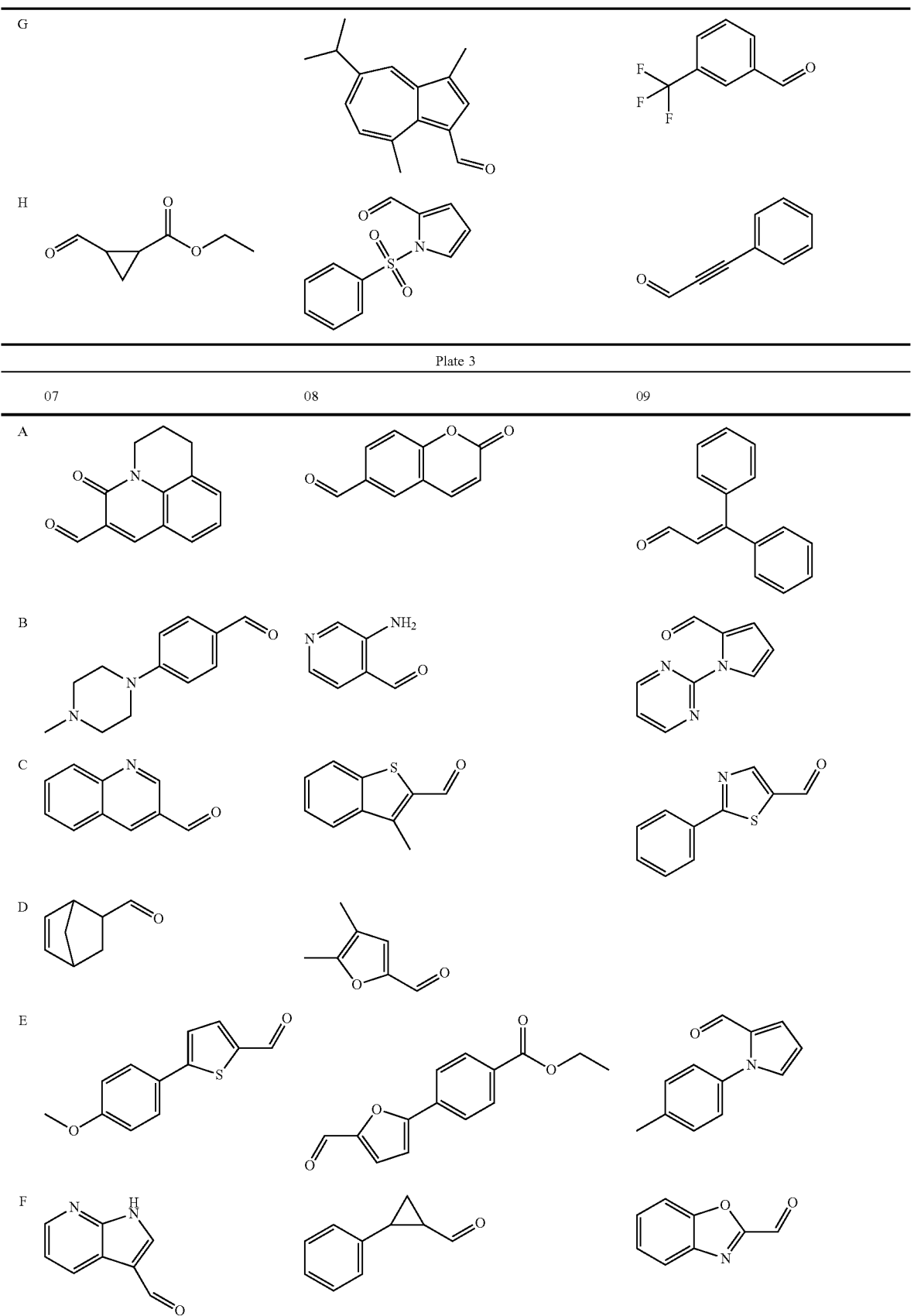

TABLE A-continued
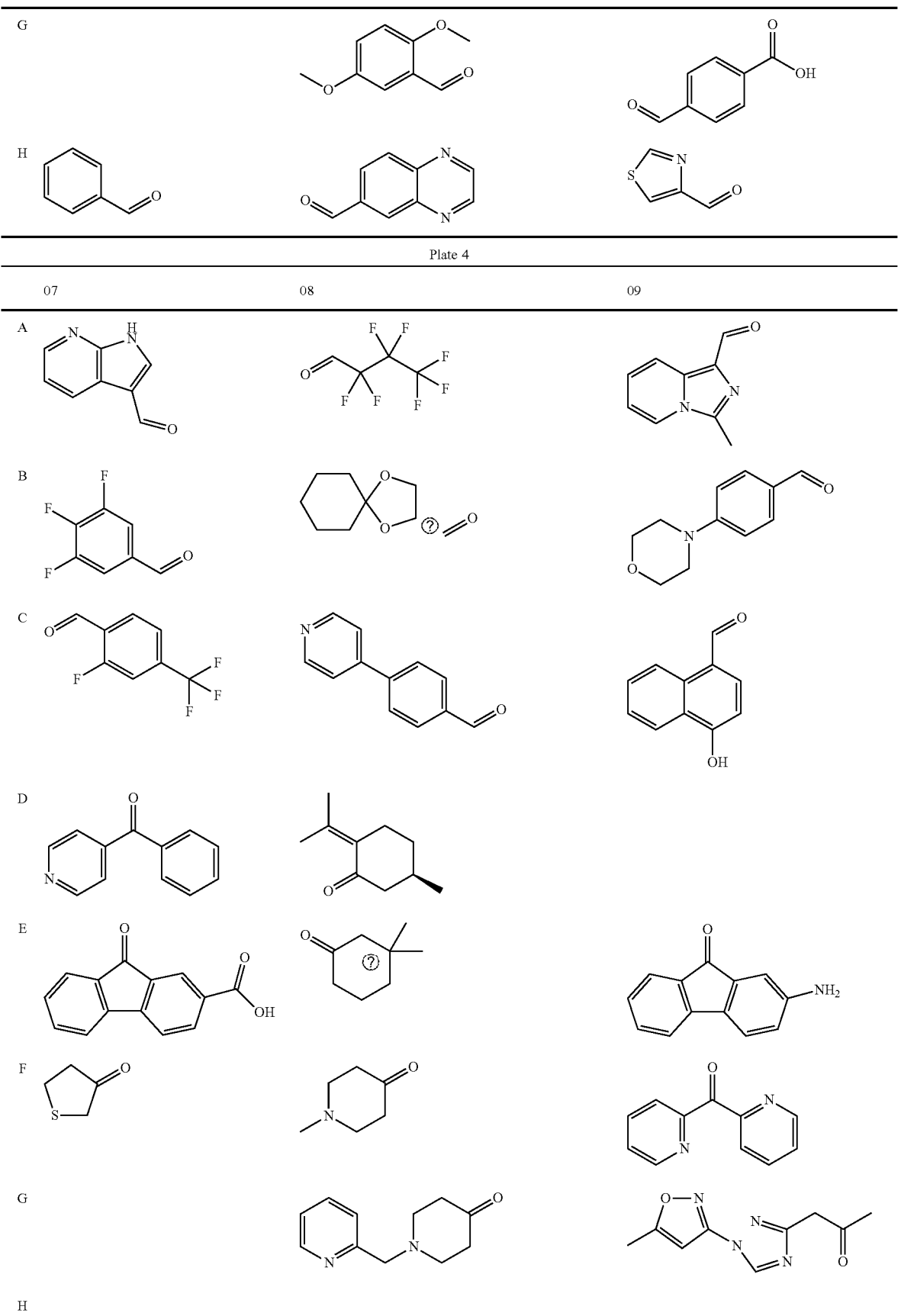

TABLE A-continued
Plate 1
| | 10 | 11 | 12 |
|---|---|---|---|
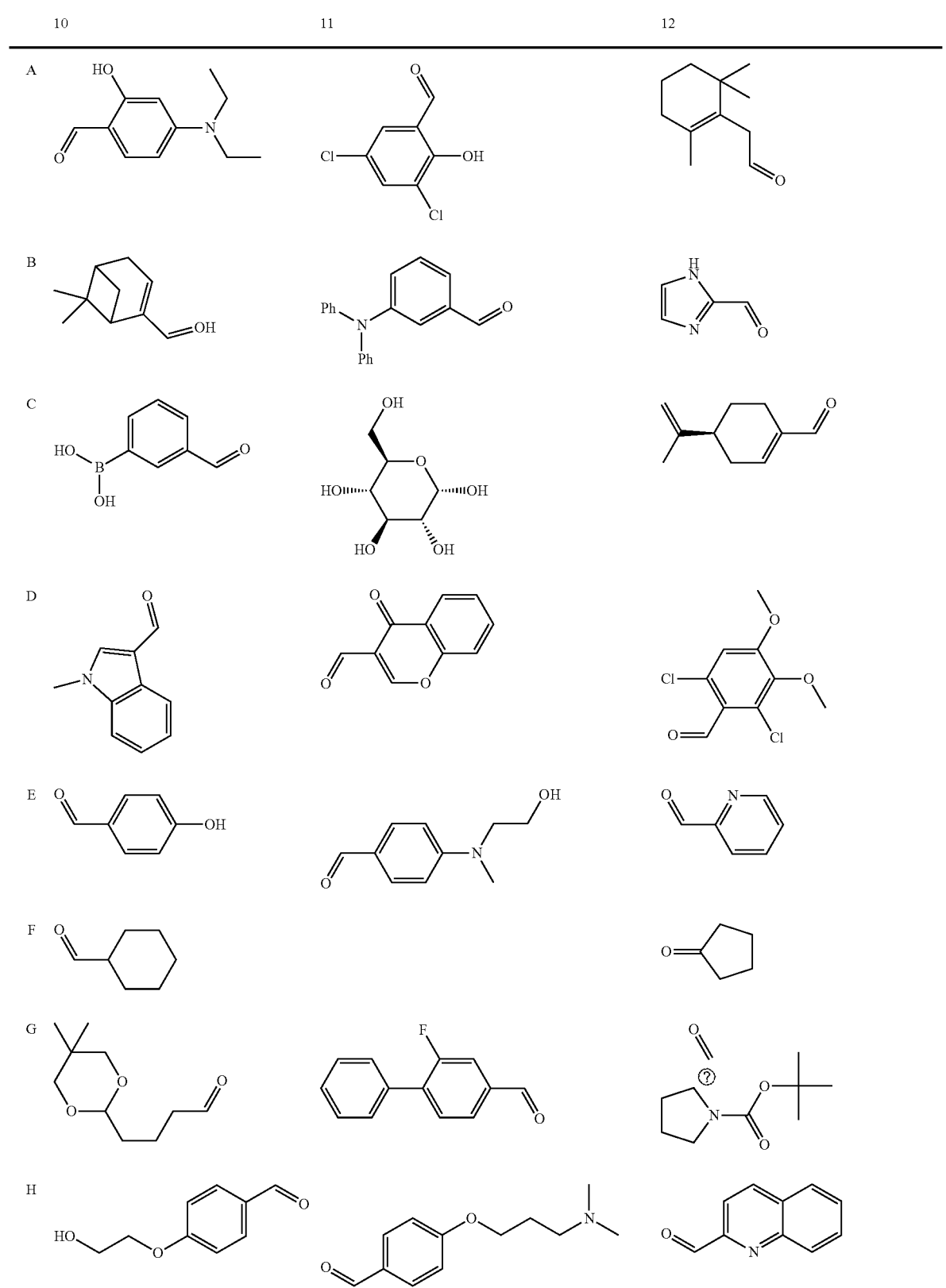

TABLE A-continued
Plate 2
| | 10 | 11 | 12 |
|---|---|---|---|
| A | 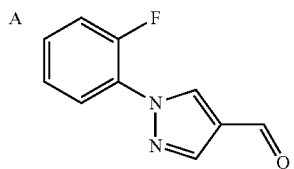 | 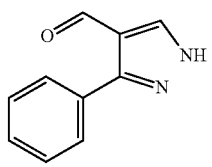 [SMILES: N=C(/C(C=O)=C\N)c1ccccc1] | 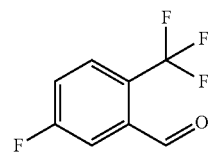 |
| B | 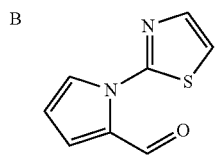 | 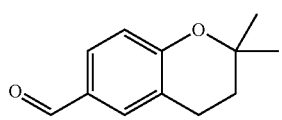 | 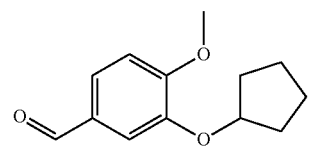 [SMILES: COc1ccc(C=O)cc1OC1CCCC1] |
| C | 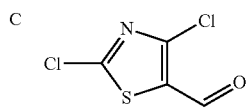 | 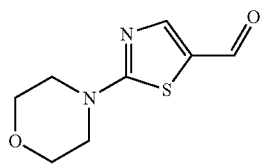 [SMILES: O=Cc1cnc(N2CCOCC2)s1] | 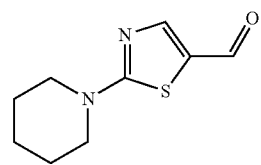 [SMILES: O=Cc1cnc(N2CCCCC2)s1] |
| D | 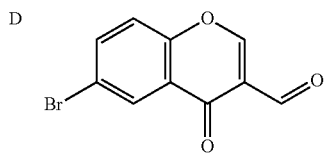 | 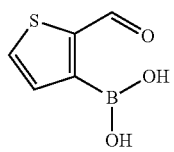 | 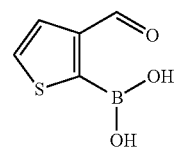 |
| E | 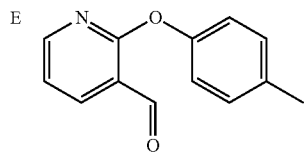 | 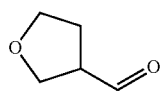 | 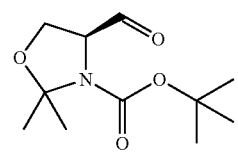 [SMILES: CC(C)(C)OC(=O)N1[C@H](C=O)COC1(C)C] |
| F | 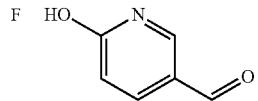 | | 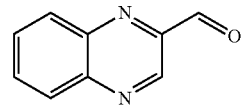 [SMILES: O=Cc1cnc2ccccc2n1] |
| G | 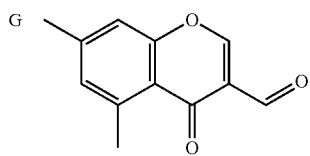 | 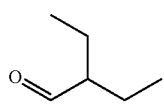 | 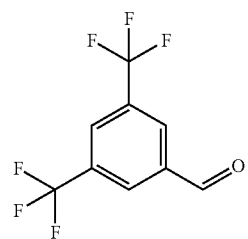 [SMILES: O=Cc1cc(C(F)(F)F)cc(C(F)(F)F)c1] |
| H | 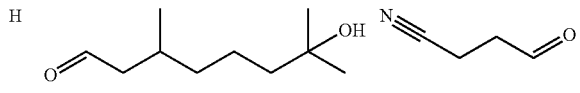 | | 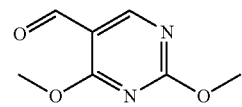 |

TABLE A-continued
Plate 3
| | 10 | 11 | 12 |
|---|---|---|---|
| A | | | |
| B | | | |
| C | | | |
| D | | | |
| E | | | |
| F | | | |
| G | | | |
| H | | | |
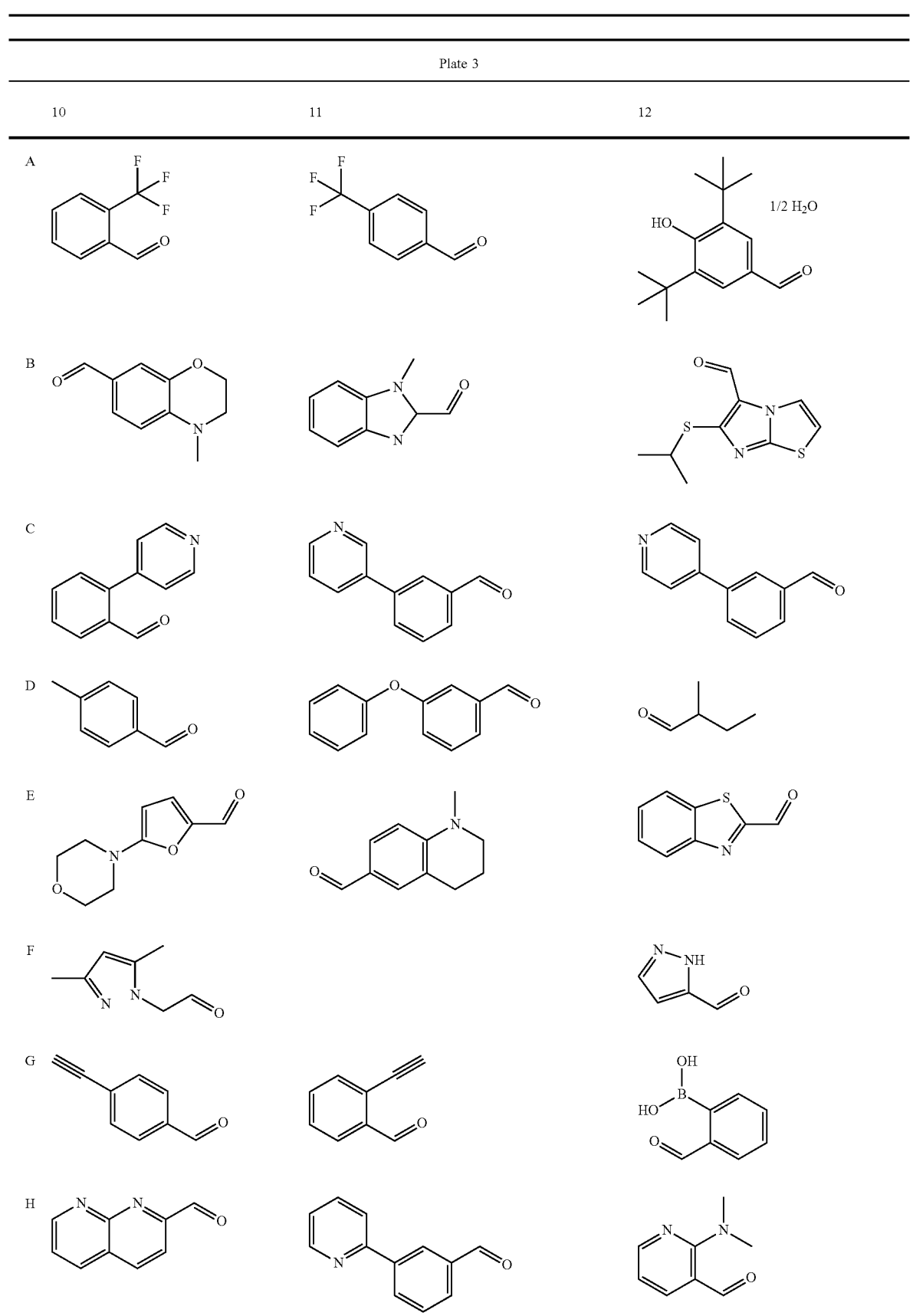

TABLE A-continued
Plate 4
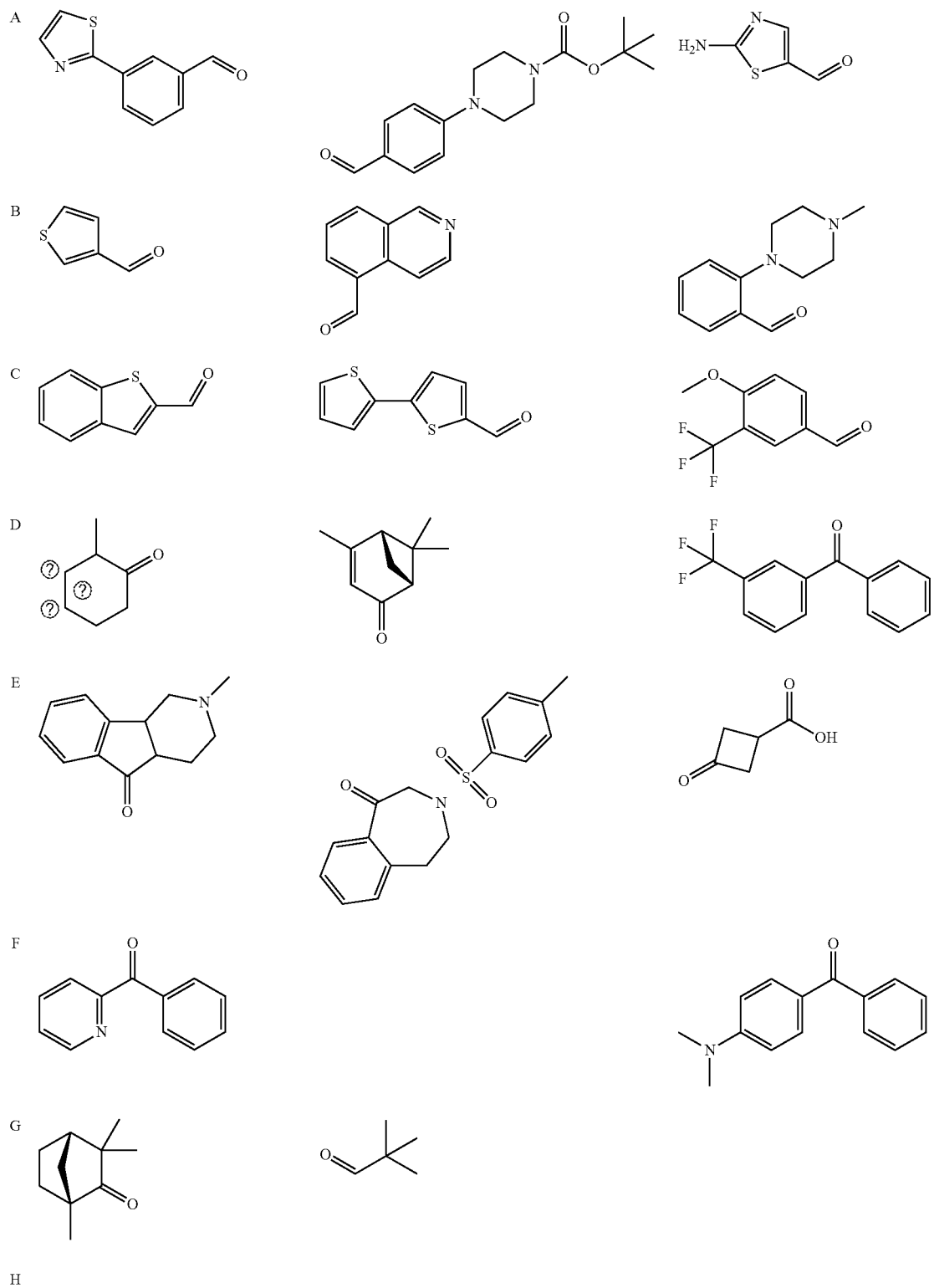

In one embodiment, the compound is a compound is represented by the formula:

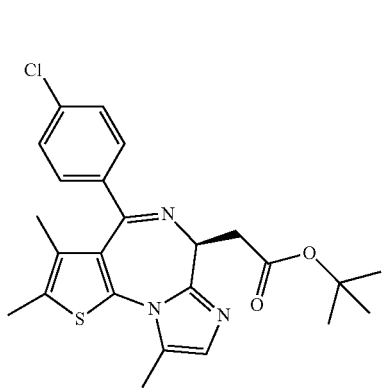 [SMILES: Cc1sc2c(c1C)C(c1ccc(Cl)cc1)=N[C@@H](CC(=O)OC(C)(C)C)c1ncc(C)n1-2]

(VIII), or a salt, solvate or hydrate thereof In certain embodiments, the compound is (racemic) JQ1; in certain embodiments, the compound is (+)-JQ1. In certain embodiments, the compound is a compound selected from the group consisting of:

(3)

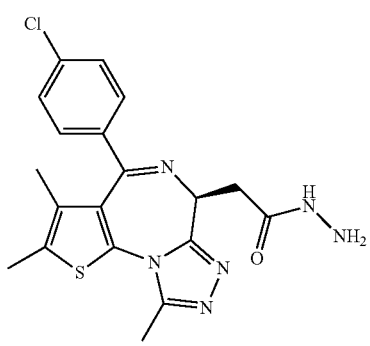

(4)

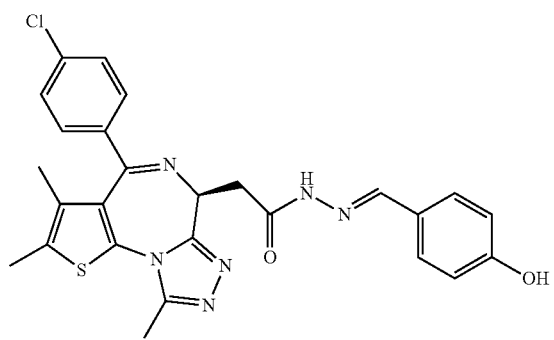

or a salt, solvate, or hydrate thereof.

Additional examples of compounds include compounds according to any of the follow formulae:

(IX)

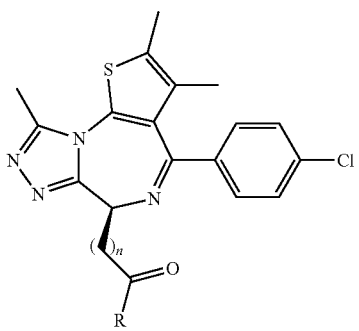

n = 1, 2, 3

(X)

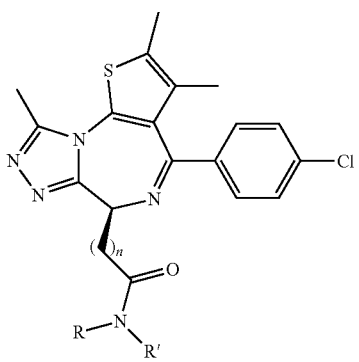

n = 1, 2, 3

(XI)

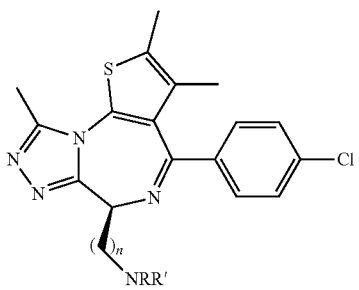

n = 1, 2, 3

(XII)

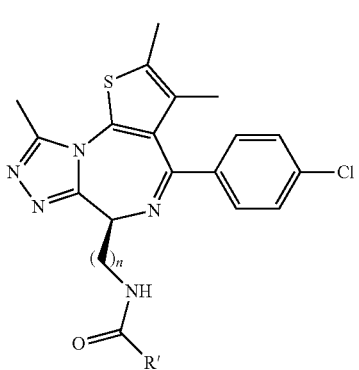

n = 1, 2, 3

-continued
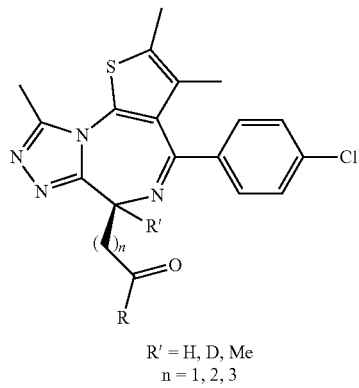
(XIII)
R' = H, D, Me
n = 1, 2, 3
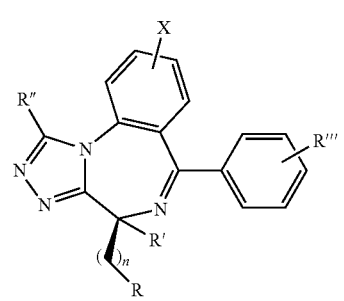
(XIV)
R' = H, D, Me
n = 1, 2, 3
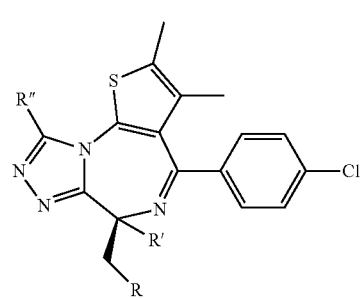
(XV)
R″ = OMe, CH₂OH, CH₂NH₂, CH₂OMe
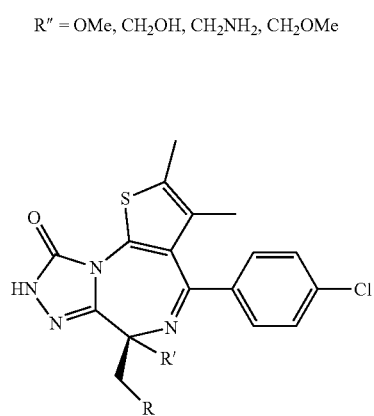
(XVI)
-continued
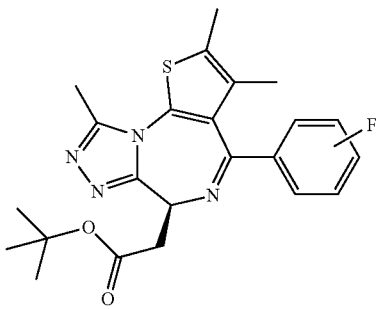
(XVII)
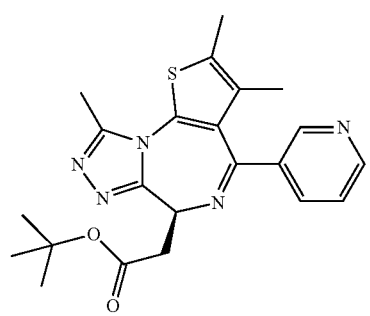
(XVIII)
Also 2- and 4-pyridyl
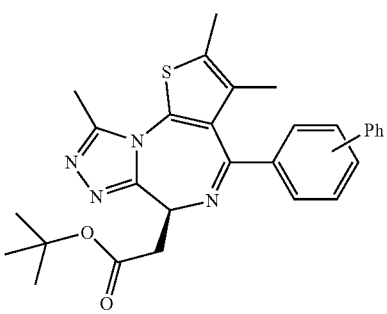
(XIX)
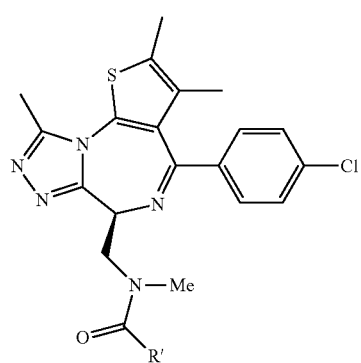
(XX)

-continued (XXI)

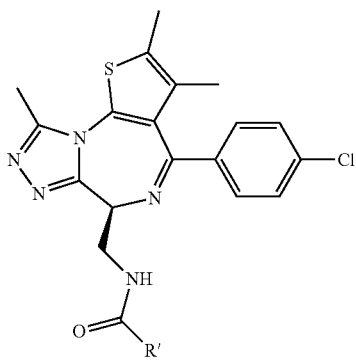

(XXII)

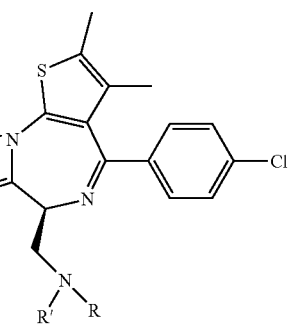

or a salt, solvate, or hydrate thereof.

In Formulae IX-XXII, R and R' can be, e.g., H, aryl, substituted aryl, heteroaryl, heteroaryl, heterocycloalkyl, —$C_1$-$C_8$ alkyl, —$C_2$-$C_8$ alkenyl, —$C_2$-$C_8$ alkynyl, —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted. In Formulae XIV, X can be any substituent for an aryl group as described herein.

In some aspects, the BET inhibitors is a compound of the following formula:

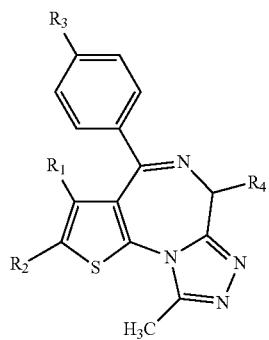

wherein $R_1$ is alkyl having a carbon number of 1-4, $R_2$ is a hydrogen atom; a halogen atom; or alkyl having a carbon number of 1-4 optionally substituted by a halogen atom or a hydroxyl group, $R_3$ is a halogen atom; phenyl optionally substituted by a halogen atom, alkyl having a carbon number of 1-4, alkoxy having a carbon number of 1-4 or cyano; —$NR_5$—$(CH_2)_m$—$R_6$ wherein $R_5$ is a hydrogen atom or alkyl having a carbon number of 1-4, m is an integer of 0-4, and $R_6$ is phenyl or pyridyl optionally substituted by a halogen atom; or —$NR_7$—CO—$(CH_2)_n$—$R_8$ wherein $R_7$ is a hydrogen atom or alkyl having a carbon number of 1-4, n is an integer of 0-2, and $R_8$ is phenyl or pyridyl optionally substituted by a halogen atom, and $R_4$ is —$(CH_2)_a$—CO—NH—$R_9$ wherein a is an integer of 1-4, and $R_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR_{10}$ wherein b is an integer of 1-4, and $R_{10}$ is alkyl having a carbon number of 1-4, or a pharmaceutically acceptable salt thereof or a hydrate or solvate thereof.

In some examples, $R_1$ is methyl.

In some examples, $R_2$ is a halogen atom (e.g., chlorine), methyl, or hydroxymethyl.

In some examples, $R_3$ is a halogen atom, methoxyphenyl, cyanophenyl, —$NR_5'$—$(CH_2)_m'$—$R_6'$ wherein $R_5'$ is a hydrogen atom or methyl, m' is 0 or 1, and $R_6'$ is phenyl, pyridyl or phenyl substituted by a fluorine atom and —$NR_7'$—CO—$(CH_2)n'$-$R_8'$ wherein $R_7'$ is a hydrogen atom, n' is 2, and $R_8'$ is phenyl, and more preferable examples include a chlorine atom, cyanophenyl, phenylamino and phenethylcarbonylamino. Most preferable examples include a chlorine atom and 3-cyanophenyl.

In some examples, $R_4$ is —$(CH_2)_{a'}$—CO—NH—$R_9'$ wherein a' is 1, and $R_9$, is methyl, hydroxyethyl, methoxy, aminophenyl, hydroxyphenyl, pyridyl or methoxypyridyl and —$(CH_2)_{b'}$—$COOR_{10}$, wherein b' is 1, and $R_{10}'$ is methyl or ethyl, such as hydroxyphenylaminocarbonylmethyl and methoxycarbonylmethyl. Other examples include 4-hydroxyphenylaminocarbonylmethyl and methoxycarbonylmethyl. In addition, the carbon atom to which $R_4$ is bonded is an asymmetric carbon atom. The steric configuration thereof may be any of S configuration, R configuration and a mixture thereof, and S configuration is desirable.

In some aspects, the BET inhibitors is include (S)-2-[4-(4-chlorophenyl)-2,3,9-trimethyl -6H-thieno[3,2-f][1,2,4]triazolo[4,3-a][1,4]diazepin-6-yl]-N-(4-hydroxyphenyl)acetamide and a dihydrate thereof.

In some aspects, the BET inhibitors is methyl (S)-{4-(3'-cyanobiphenyl-4-yl)-2,3,9-trimethyl -6H-thieno[3,2-f][1,2, 4]triazolo[4,3-a][1,4]diazepin-6-yl}acetate.

In some aspects, the BET inhibitors is methyl (S)-{2,3, 9-trimethyl-4-(4-phenylaminophenyl)-6H-thieno[3,2-f][1,2, 4]triazolo[4,3 -a][1,4]diazepin-6-yl}acetate.

In some aspects, the BET inhibitors is methyl (S)-{2,3, 9-trimethyl-4-[4-(3-phenylpropionylamino)phenyl]-6H-thieno[3,2-f][1,2,4]triazolo[4,3-a][1,4]diazepin-6-yl}acetate.

In some aspects, the BET inhibitors is (S)-2-[4-(4-chlorophenyl)-2,3,9-trimethyl-6H-thieno[3,2-f][1,2,4]triazolo[4, 3-a][1,4]diazepin-6-yl]-N-(4-hydroxyphenyl)acetamide or a dihydrate thereof.

In some aspects, the BET inhibitors is a compound of the following formula:

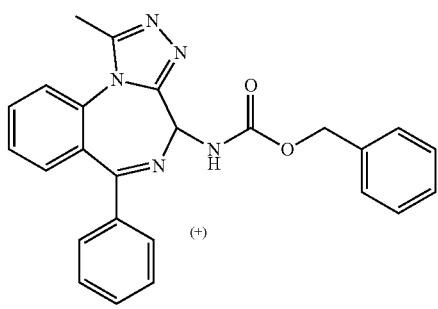 [SMILES: Cc1nnc2n1-c1ccccc1C(c1ccccc1)=NC2NC(=O)OCc1ccccc1]

(+)

In some aspects, the BET inhibitors is a compound of the following formula:

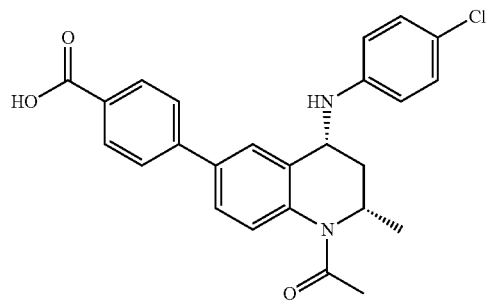 [SMILES: CC(=O)N1c2ccc(-c3ccc(C(=O)O)cc3)cc2[C@H](Nc2ccc(Cl)cc2)C[C@@H]1C]

In some aspects, the BET inhibitors is a compound of the following formula:

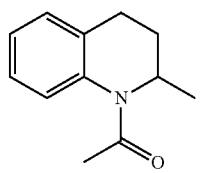

In some aspects, the BET inhibitors is a compound of the following formula:

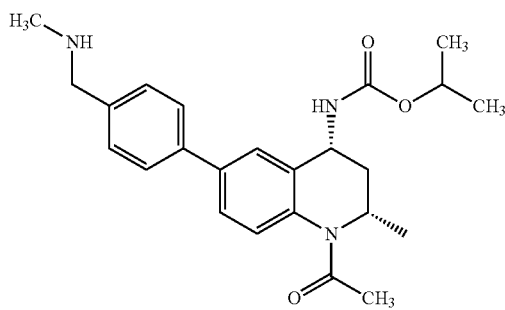 [SMILES: CNCc1ccc(-c2ccc3c(c2)[C@H](NC(=O)OC(C)C)C[C@H](C)N3C(C)=O)cc1]

In some aspects, the BET inhibitors is a compound of the following formula:

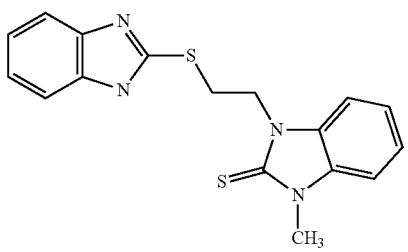 [SMILES: Cn1c(=S)n(CCSc2nc3ccccc3[nH]2)c2ccccc21]

In some embodiments, the BET inhibitor is a small molecule compound that binds to the binding pocket of the first bromodomain of a BET family member (e.g., BRD1, BRD2, BRD3, BRD4, BRD7, BRDT; see WO 2011143669). In some important embodiments, the BET inhibitor is JQ 1 and has the formula below:

JQ1

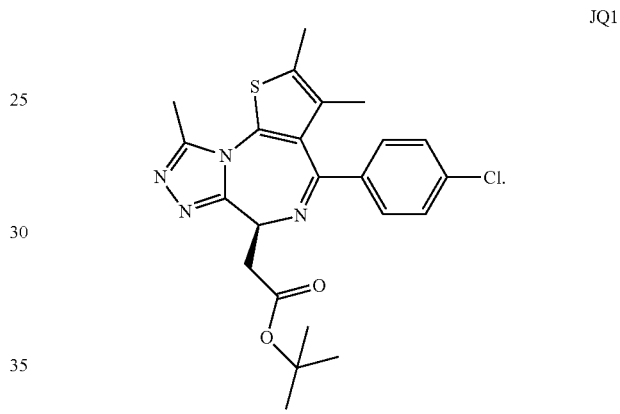

The disclosed bromodomain inhibitors can be used in combination with a cancer immunotherapy. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

In order to actively drive an antitumor immune response, therapeutic cancer vaccines have been developed. Unlike the prophylactic vaccines that are used preventatively to treat infectious diseases, therapeutic vaccines are designed to treat established cancer by stimulating an immune response against a specific tumor-associated antigen. In 2010, sipuleucel-T (Provenge; Dendreon Corporation) was approved by the FDA for the treatment of metastatic, castration-resistant prostate cancer based on the results of the IMPACT (Immunotherapy Prostate Adenocarcinoma Treatment) trial in which it improved OS by 4.1 months and reduced the risk of death by 22% versus placebo. The advantage of active immunotherapies is that they have the potential to provide long-lasting anticancer activity by engaging both the innate and adaptive arms of the immune response. While mAbs are typically considered passive immunotherapies, there is increasing evidence that they also induce an adaptive immune response via a "vaccination-like" effect.

The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. A list of immune-checkpoint targeting antibodies in clinical trials is provided in Table 1.

TABLE 1

Clinically evaluated immune-checkpoint blocking antibodies

| Target | Antibody |
|---|---|
| CTLA-4 | Ipilimumab (MDX-010) |
| | Tremelimumab (CP-675,206) |
| PD1 | Nivolumab (BMS-936558 or MDX1106) |
| | CT-011 |
| | MK-3475 |
| PDL1 | MDX-1105 (BMS-936559) |
| | MPDL3280A |
| | MSB0010718C |
| PDL2 | rHIgM12B7 |
| B7-H3 | MGA271 |
| LAG3 | BMS-986016 |

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

Also disclosed is a composition, e.g., a pharmaceutical composition, containing a bromodomain inhibitor, formulated together with a pharmaceutically acceptable carrier. Pharmaceutical compositions can be administered in combination therapy, i.e., combined with other agents. For example, the combination therapy can include a bromodomain inhibitor antibody combined with at least one other anti-inflammatory or immunosuppressant agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The disclosed pharmaceutical composition may include one or more pharmaceutically acceptable salts. A "pharmaceutically acceptable salt" refers to a salt that retains the desired biological activity of the parent compound and does not impart any undesired toxicological effects.

The disclosed pharmaceutical composition may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the bromodomain inhibitor, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for a bromodomain inhibitor include 1 mg/kg body weight or 3 mg/kg body weight via intravenous administration, with the bromodomain inhibitor being given using one of the following dosing schedules: (i) every four weeks for six dosages, then every three months; (ii) every three weeks; (iii) 3 mg/kg body weight once followed by 1 mg/kg body weight every three weeks.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition disclosed herein can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the composition can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

T cell activation can be induced either ex vivo or in vivo by autologous dendritic cells or artificial antigen-presenting cells (aAPCs), or by engineering of T cells through transgenic delivery of T cell receptors (TCRs). Ex vivo-activated autologous T cells can be adoptively transferred into patients to specifically kill cancer cells. Therefore, also disclosed is a method for ex vivo activation and expansion of antigen-specific T cells for adoptive cell transfer (ACT). The method involves exposing a population of antigen presenting cells (APC) to a population of T lymphocytes in the presence of a bromodomain inhibitor under conditions suitable to activate and expand antigen-specific T cells. For example, the T lymphocytes can be selected from the group consisting of autologous tumor-infiltrating lymphocytes (TIL), T cells transduced with high-affinity T cell receptors (TCR), and T cells transduced with chimeric antigen receptors (CAR).

Alternatively, injection of APCs can lead to in vivo immunotherapy without the need for autologous cell cultures. Therefore, also disclosed is a method for enhancing the function of APCs ex vivo for in vivo immunotherapy. The method involves contacting a population of antigen presenting cells (APC) with a bromodomain inhibitor.

APCs that can be used in the disclosed methods include autologous dendritic cells, macrophages, or a combination thereof.

A number of embodiments of the invention have been described. Nevertheless, it will be understood that various modifications may be made without departing from the spirit and scope of the invention. Accordingly, other embodiments are within the scope of the following claims.

EXAMPLES

Example 1

JQ 1, a Selective Bromodomain Inhibitor, Decreased the Expression of the Tolerogenic Molecule PDL1 in Antigen-Presenting Cells (APCs) and Restores the Responsiveness of Anergic CD4+ T Cells Bromodomain and extraterminal (BET) is a protein domain that recognizes acetylated lysine residues such as those on the N-terminal tails of histones. This recognition is often a prerequisite for protein-histone association, chromatin remodeling and gene transcription. The role of BET proteins in regulating the response of inflammatory cytokine genes through translation of histone marks was poorly understood.

Given that the inflammatory status of the APC is critical in determining T-cell activation versus T-cell tolerance and that epigenetic modifications of specific genes in the APC play a key role in this process, the functional consequences of inhibiting BET in APCs was determined.

Materials and Methods

In order to determine the best working concentration of JQ1 in PEM, plated PEM (96-well plate) were treated with increased concentration of JQ1 for 24 hours then cell viability was determined. A threshold of 100 to 800 nanomolar was determined to be acceptable.

Macrophages (PEM) were treated with different concentrations of JQ1 in presence and absence of LPS (stimulant for macrophages). After 24 hours, supernatant was collected and IL-10 & IL-6 production was determined by ELISA. There was decreased production of both IL-10 and IL-6 production that was dose dependent. mRNA expression of IL-6 and IL-10 with either LPS or JQ1 treatment and in combination of the two was determined by real time PCR.

PEM were treated with different concentrations of JQ1 in presence and absence of LPS. Flow cytometry was performed on PEM treated with different concentrations of JQ1 in presence and absence of LPS using anti-PD-L1 and anti-PD-L2 as well as isotype as a control. Combination treatment of PEM with JQ1 & LPS showed a relatively decreased expression of PD-L1 & PD-L2 than LPS alone. mRNA expression of PD-L1 & PD-L2 after treatment LPS or JQ1 treatment and combination of the two was also determined by real time PCR. The combination treatment of PEM with LPS+JQ1 has a decreased expression of PDL1 mRNA.

PEM were treated with different concentrations of JQ1 in presence and absence of LPS. After 24 hours, PEM was washed twice with warm RPMI. Naïve CD4 T-cells or tolerant T-cells were added to the plated macrophages with or without OVA peptide and co-cultured for 48 hours. IL-2 and IFN-γ production were determined by ELISA. Without OVA peptide, there was no production of IL-2 or IFN-γ. There is an increase in dose dependent production of both IL-2 and IFN-gamma by CD4 T-cell. Combination treatment (JQ1+LPS) of PEM resulted in enhanced IFN-gamma production by tolerant T-cells.

Therefore, not only is there an increase in antigen presenting capability in Naïve CD4 T-cells, but more importantly there's a restoration of tolerant T-cell function after treatment with JQ1. Therefore, APCs treated with BDR specific inhibitor JQ1 are more inflammatory and display decreased expression of immunosuppressive molecule PD-L1. BET inhibitors such as JQ1 are therefore capable of restoring responsiveness of tolerant T-cells and have promising therapeutic applications and broadened clinical scope.

Results

Figure 2:
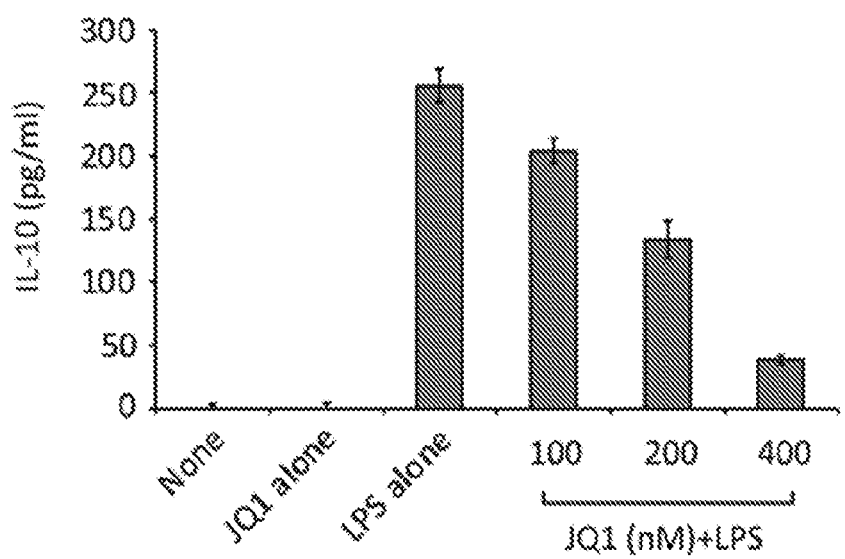
FIG. 2 shows IL-10 production (pg/ml) by peritoneal elicited macrophages (PEM) after treatment with JQ1 (100, 200 or 400 nM) with and without LPS.
Figure 3:
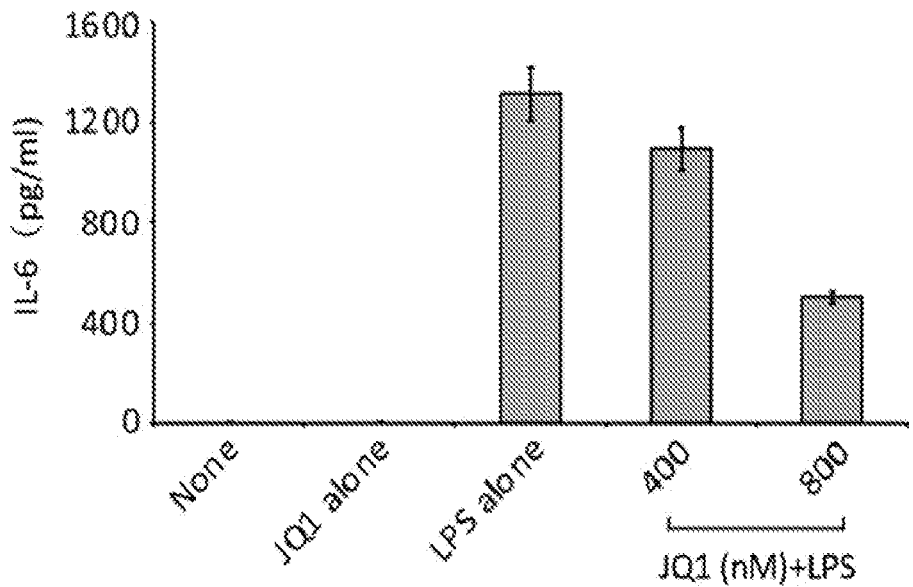
FIG. 3 shows IL-6 production (pg/ml) by PEM after treatment with JQ1 (400 or 800 nM) with and without LPS.
Figure 4:
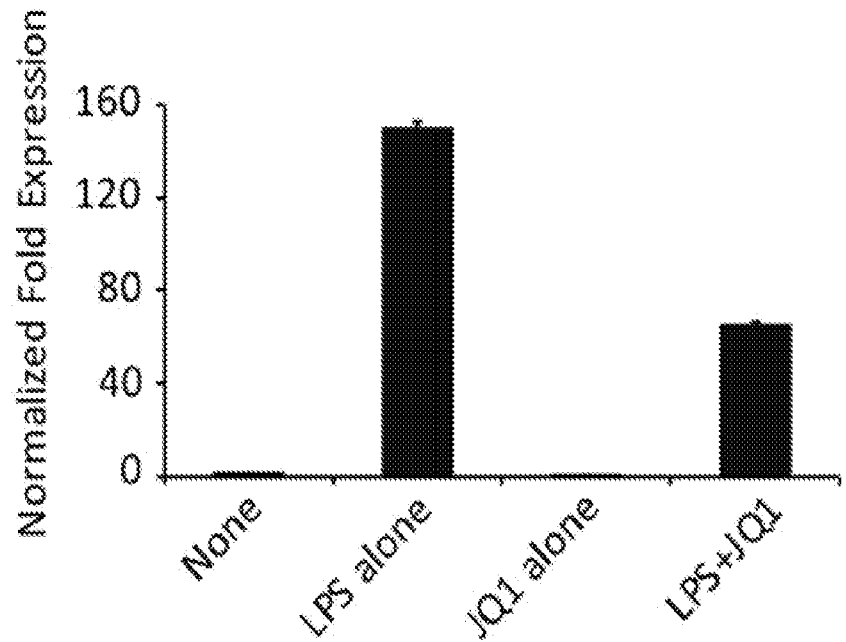
FIG. 4 shows IL-6 and IL10 mRNA expression (normalized fold expression) in PEM after treatment with JQ1, LPS, or JQ1 and LPS.
Figure 5:
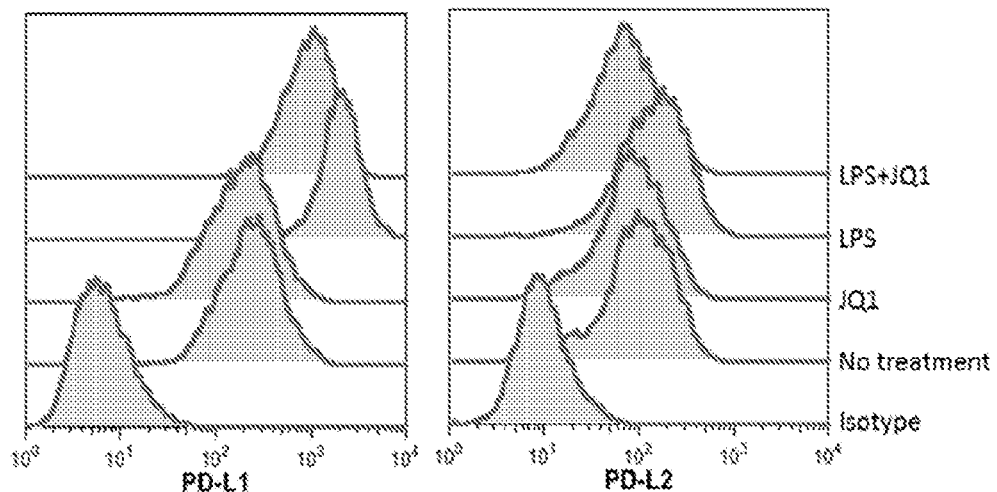
FIG. 5 shows flow cytometry results of PEM treated with isotype, nothing, JQ1, LPS, or JQ1 and LPS using anti-PD-L1 (left) or anti-PD-L2 (right) antibodies.
Figure 6:
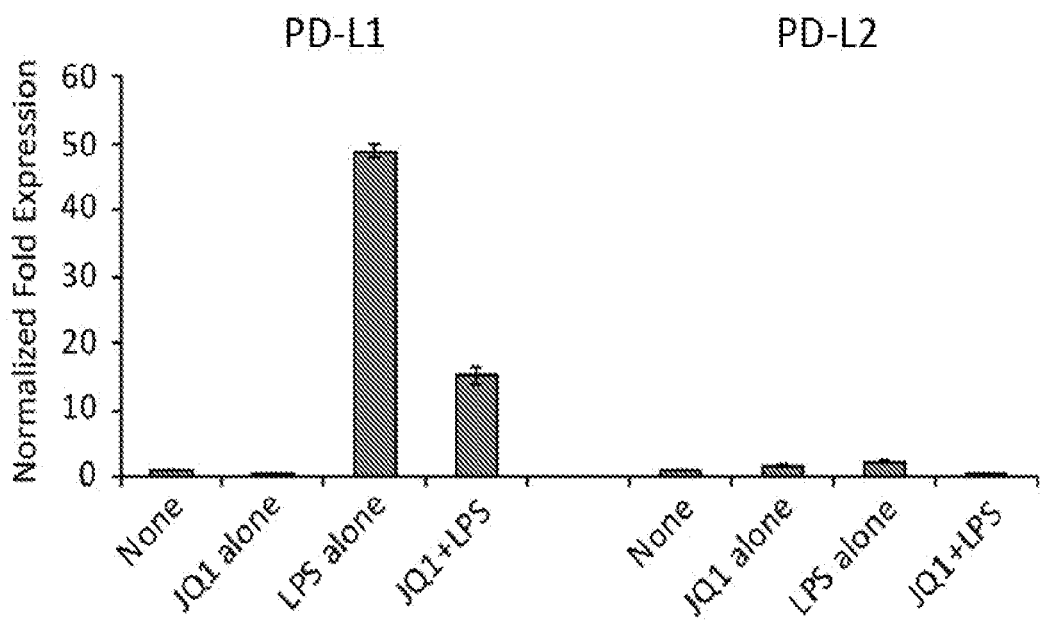
FIG. 6 shows PD-L1 and PD-L2 mRNA expression in PEM treated with nothing, JQ1, LPS, or JQ1 and LPS.
Figure 7:
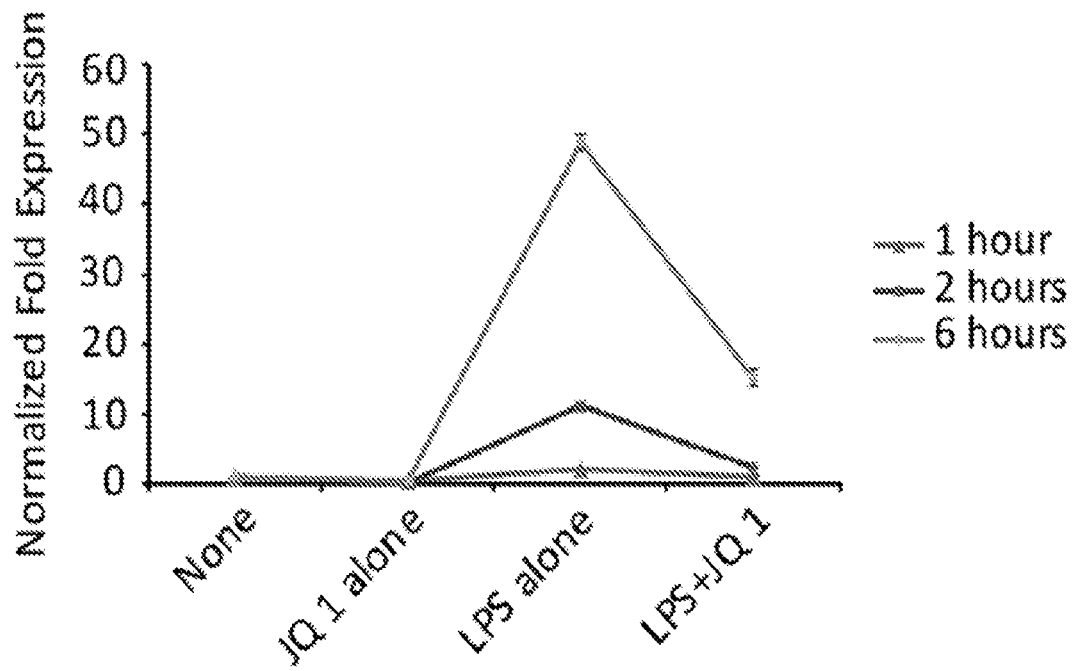
FIG. 7 shows PD-L1 mRNA expression in PEM treated with nothing, JQ1, LPS, or JQ1 and LPS at 1, 2, and 6 hours after treatment.
Figure 8:
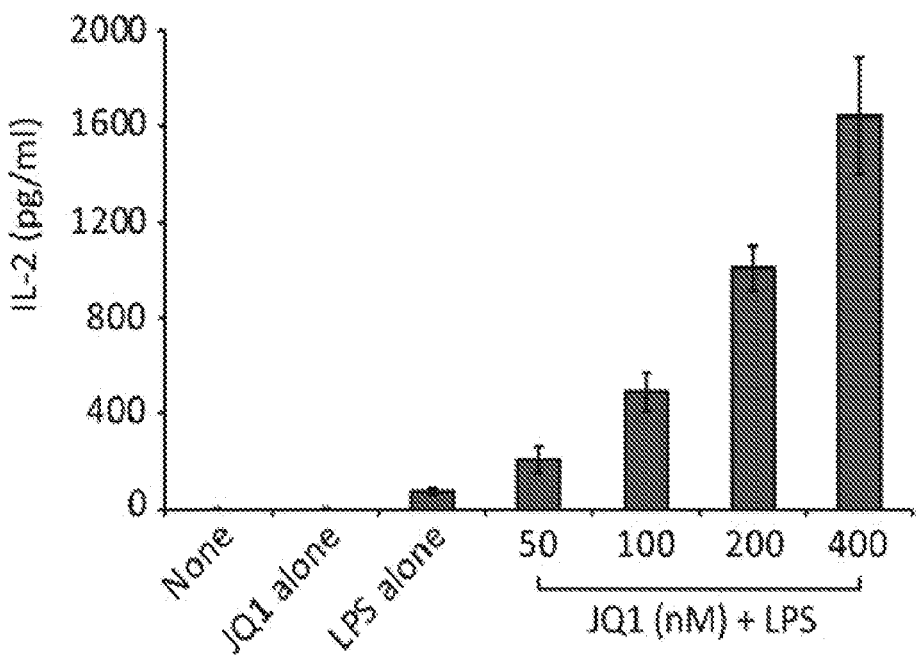
FIG. 8 shows IL-2 production (pg/ml) by PEM treated with JQ1, LPS, or JQ1 and LPS for 24 hours and then cultured with naïve CD4 T-cells with or without OVA peptide for another 48 hours.
Figure 9:
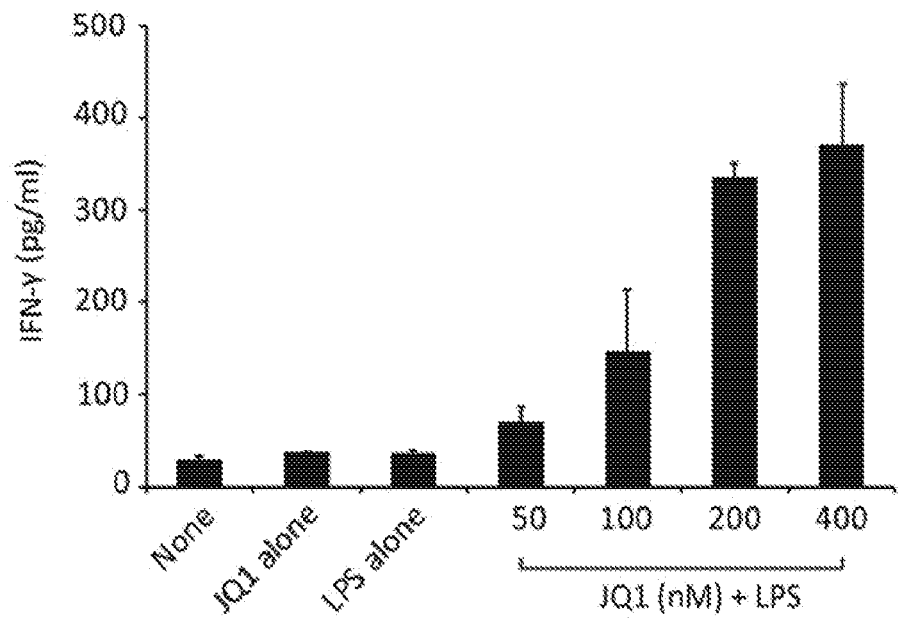
FIG. 9 shows INF-γ production (pg/ml) by PEM treated with JQ1, LPS, or JQ1 and LPS for 24 hours and then cultured with naïve CD4 T-cells with or without OVA peptide for another 48 hours.
Figure 10:
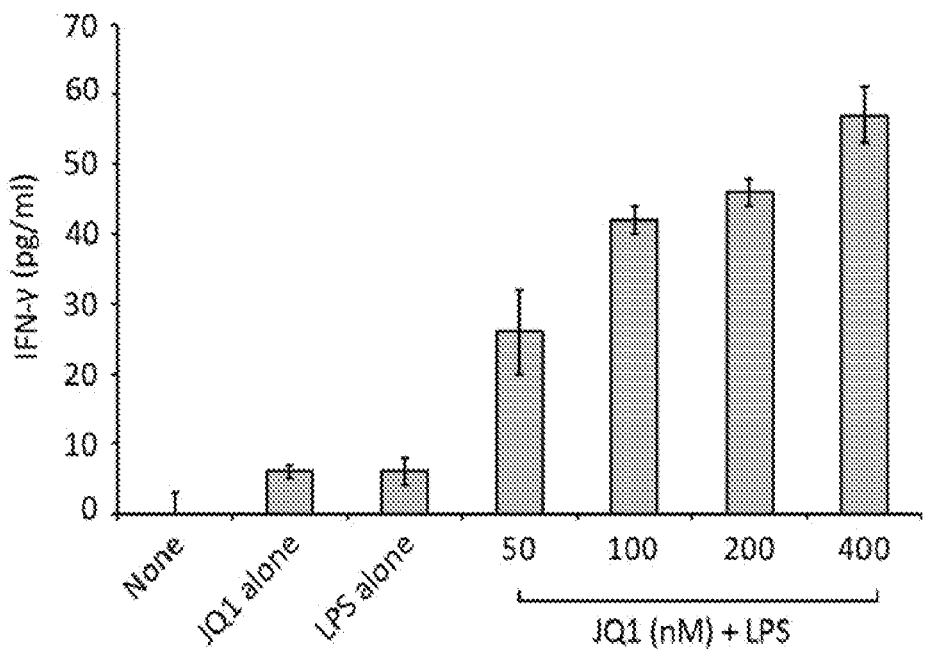
FIG. 10 shows INF-γ production (pg/ml) by PEM treated with JQ1, LPS, or JQ1 and LPS for 24 hours and then cultured with tolerant CD4 T-cells with or without OVA peptide for another 48 hours.

First, the effects of JQ1, a selective small-molecule BET bromodomain inhibitor, on APC's function and its regulation of antigen-specific CD4+ T-cells response was evaluated. In vitro treatment of peritoneal elicited macrophages (PEM) or bone marrow derived dendritic cells (DCs) with increasing concentrations of JQ 1 resulted in decreased expression and protein production of the anti-inflammatory cytokine IL-10 and IL-6 in response to LPS stimulation (FIGS. 2 to 4). At the concentration used, JQ 1 did not affect the viability of treated APCs (FIG. 1). Second, analysis of the expression of MHC class molecules and co-stimulatory molecules revealed a decreased expression of the tolerogenic PDL1 molecule in JQ 1—treated APCs as compared to untreated APCs (FIGS. 5 to 7). Third, the ability of JQ 1 treated APCs to present cognate antigen to naïve or tolerant antigen-specific CD4+ T-cells was evaluated. Treatment of either PEM or DC with JQ 1 enhanced their antigen-presenting capabilities leading to effective priming of naïve CD4+ T-cells confirmed by their increased production of IL-2 (FIG. 8) and IFN-gamma (FIG. 9) in response to cognate antigen. More importantly, JQ 1- treated APCs were able to restore the responsiveness of tolerant CD4+ T-cells isolated from lymphoma bearing hosts (FIG. 10).

Taken together, APCs treated with the Bromodomain specific inhibitor JQ 1 are more inflammatory, display lower expression of the immunosuppressive molecule PDL1 and more importantly, are capable of restoring the responsiveness of tolerant T-cells. These results have unveiled a previously unknown immunological effect of BET inhibitors and have broadened their clinical scope as promising adjuvants in cancer immunotherapy.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for ex vivo activation and expansion of antigen-specific T cells for adoptive cell transfer (ACT), comprising exposing a population of antigen presenting cells (APC) to a population of T lymphocytes in the presence of a bromodomain inhibitor, wherein the bromodomain inhibitor comprises the following chemical formula:

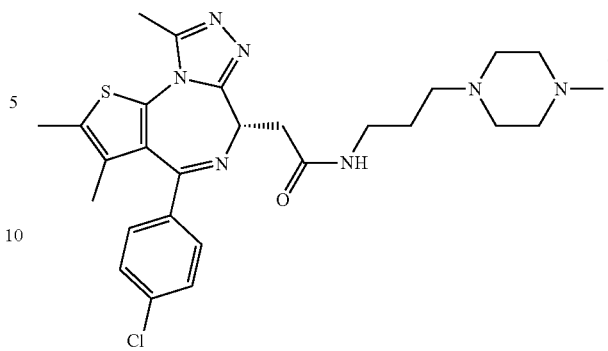

2. The method of claim 1, wherein the T lymphocytes are selected from the group consisting of autologous tumor-infiltrating lymphocytes (TIL), T cells transduced with high-affinity T cell receptors (TCR), and T cells transduced with chimeric antigen receptors (CAR).

3. The method of claim 1, wherein the APCs comprise autologous dendritic cells, macrophages, or a combination thereof.

* * * * *